US008871455B2

(12) United States Patent
Blakely et al.

(10) Patent No.: US 8,871,455 B2
(45) Date of Patent: Oct. 28, 2014

(54) BIOMARKER PANELS FOR ASSESSING RADIATION INJURY AND EXPOSURE

(75) Inventors: William Blakely, Silver Spring, MD (US); Natalia Ossetrova, Sterling, VA (US); Marcy Grace, Gaithersburg, MD (US); Alexandra Miller, Hyattsville, MD (US); Jean Mulimbi Muderhwa, San Antonio, TX (US); Glen Manglapus, Bel Air, MD (US)

(73) Assignee: The Henry M. Jackson Foundation for the Advancement of Military Medicine, Inc., Rockville, MD (US)

( * ) Notice: Subject to any disclaimer, the term of this patent is extended or adjusted under 35 U.S.C. 154(b) by 1552 days.

(21) Appl. No.: 12/304,566

(22) PCT Filed: Jun. 12, 2007

(86) PCT No.: PCT/US2007/013752
§ 371 (c)(1),
(2), (4) Date: Jul. 23, 2009

(87) PCT Pub. No.: WO2008/140463
PCT Pub. Date: Nov. 20, 2008

(65) Prior Publication Data
US 2012/0329070 A1 Dec. 27, 2012

Related U.S. Application Data

(60) Provisional application No. 60/812,596, filed on Jun. 12, 2006.

(51) Int. Cl.
G01N 33/573 (2006.01)
G01N 33/567 (2006.01)
A61K 49/00 (2006.01)
C07K 16/24 (2006.01)
G01N 33/569 (2006.01)

(52) U.S. Cl.
CPC ........... *C07K 16/248* (2013.01); *A61K 49/0008* (2013.01); *G01N 33/56972* (2013.01); *G01N 2333/5412* (2013.01); *G01N 2333/928* (2013.01); *G01N 2333/82* (2013.01); *A61K 49/0004* (2013.01); *G01N 2800/40* (2013.01); *G01N 2333/4737* (2013.01)
USPC ......................................... 435/7.4; 435/7.92

(58) Field of Classification Search
CPC ............. C12Q 1/6809; G01N 33/6893; G01N 2800/40; G01N 2333/5412; G01N 2333/54; G01N 33/56972; G01N 33/6842; A61B 5/08; A61B 5/082; A61B 5/0836; A61B 5/087; A61B 5/091; A61B 5/417; A61B 5/4848
See application file for complete search history.

(56) References Cited

U.S. PATENT DOCUMENTS

| 4,208,479 | A  | * | 6/1980  | Zuk et al. ........................ 435/7.9 |
| 2002/0188277 | A1 |   | 12/2002 | Roorda et al. |
| 2004/0126801 | A1 |   | 7/2004  | Fiscella et al. |
| 2005/0101841 | A9 |   | 5/2005  | Kaylor et al. |
| 2006/0013801 | A1 |   | 1/2006  | Okunieff et al. |

FOREIGN PATENT DOCUMENTS

WO    WO03/072050    *    9/2003

OTHER PUBLICATIONS

Blakely et al., (Adv. Space Res. vol. 31, No. 6, pp. 1487-1493).*
Hayashi et. al., (Int. J. Radiat. Biol. 2003; vol. 79 No. 2, 129-136).*
Gramantieri et al., (Hum Pathol. Nov. 2005;36(11):1154-62. Epub Oct. 10, 2005, Abstract.*
Fedorocko et al., (Int. J. Radiat. Biol. 2002, vol. 78, No. 4, 305-31).*
Maltsev et al., (Radiats Biol Radioecol. Mar.-Apr. 2006;46(2):152-8, English translation included).*
Bertho et al., (Radioprotection 2001;vol. 36, No. 3,pp. 303-315, English Abstract ).*
Blaydes et al., (Methods of Biology;1999,vol. 113,p. 591-598).*
Prasanna et al., (RTO HFM Symposium on "NATO Medical Surveillance and Response, Research and Technology Opportunities and Options", held in Budapest, Hungary, Apr. 19-21, 2004, and published in RTO-MP-HFM-108, figures 1, 3 and whole article).*
Becciolini et al. "Effects of irradiation with conventional and multiple daily fractionation on serum amylase activity." Acta Oncologica 26(2): 139-142 (1987) (4 pages).
Becciolini et al. "Plasma amylase activity as a biochemical indicator of radiation injury to salivary glands." Acta Radiol. Oncol. 23(1): 9-14 (1984) (1 page).
Becciolini et al. "Proposal for biochemical dosimeter for prolonged space flights." Phys. Med. 17 (Suppl. 1): 185-186 (2001) (2 pages).

(Continued)

*Primary Examiner* — Shafiqul Haq
*Assistant Examiner* — Carmencita M Belei
(74) *Attorney, Agent, or Firm* — Foley & Lardner LLP

(57) ABSTRACT

Methods and kits are provided for assessing radiation injury and exposure in a subject. The methods comprise measuring the levels of at least two (2) protein biomarkers from different biological pathways and correlating the levels with an assessment of radiation injury and exposure. Additional use of peripheral blood cell counts and serum enzyme biomarkers, evaluated in the early time frame after a suspected radiation exposure, and use of integrated multiple parameter triage tools to enhance radiation exposure discrimination and assessment are also provided. The information obtained from such methods can be used by a clinician to accurately assess the extent of radiation injury/exposure in the subject, and thus will provide a valuable tool for determining treatment protocols on a subject by subject basis.

18 Claims, 21 Drawing Sheets

(56) References Cited

OTHER PUBLICATIONS

Becciolini et al. "Radiation effects on the paratid gland of mammals. Part 4: Biochemical and morphological changes after local irradiation." Strahlentherapie 156(1): 69-72 (1980) (4 pages).
Bellidio et al. "Transcriptional activation of the p21 (WAF1, CIP1, SDI1) gene by interleukin-6 type cytokines. A prerequisite for their pro-differentiating and anti-apoptotic effects on human osteoblastic cells." J. Biol. Chem. 273(33): 21137-21144 (1998) (8 pages).
Bertho et al. "Level of Flt3-ligand in plasma: a possible new bio-indicator for radiation-induced aplasia." Int. J. Radiat. Biol. 77(6) 703-712 (2001) (10 pages).
Blakely et al. "Early-response biological dosimetry-recommended countermeasure enhancements for mass-casualty radiological incidents and terrorism." Health Physics 89:5, 494-504 (2005) (11 pages).
Chen et al. "Radiation-induced change in serum and urinary amylase levels in man." Radiation Research 54(1):141-151 (1973) (11 pages).
Cozzi et al. "Overexpression of wild type and mutated human ferritin H-chain in HeLa cells: in vivio role of ferritin ferroxidase activity." J. Biol. Chem. 275(33): 25122-25129 (2000) (8 pages).
Dainiak et al. "Hematologic consequences of exposure to ionizing radiation." Exp. Hematol. 30, 513-528 (2002) (16 pages).
Gartel et al. "The role of the cyclin-dependent kinase inhibitor p21 in apoptosis." Molecular Cancer Therapeutics 1, 639-649 (2002) (11 pages).
Goltry et al. "Induction of serum amyloid a inflammatory response genes in irradiated bone marrow cells." Radiation Research 149, 570-578 (1998) (9 pages).
Hoffman et al. "Increased serum amylase in patients after radiotherapy as a probable bioindicator for radiation exposure." Strahlenther. Onkol. 166, 688-695 (1990) (8 pages).
PCT US/07/13752 International Search Report, mailed Sep. 22, 2008 (2 pages).
Kalechman et al. "Induction of acute phase proteins in mice and humans by treatement with AS101, an immunomodulator with radioprotective properties." Immunopharmacology 29, 149-158 (1995) (10 pages).
Koc et al. "Levels of some acute-phase proteins in the serum of patients with cancer during radiotherapy." Biol. Pharm. Bull. 26 (10): 1494-1497 (2003) (4 pages).
Koziol et al. "Reference centiles for serum ferritin and percentage of transferrin saturation, with application to mutations of the HFE gene." Clin. Chem. 47(10):1804-1810 (2001) (7 pages).
Larsson et al. "Increased serum concentrations of carbohydrate-deficient transferrin (CDT) in patients with cystic fibrosis." Ups. J. Med. Sci. 103, 231-236 (1998) (6 pages).
Levina et al. "Change in iron metabolism as affected by ionizing radiation." Gematol. Transfuziol. 38(9): 5-8 (1993) (4 pages).
Lipschitz et al. "A clinicial evaluation of serum ferritin as an index of iron stores." N. Eng. J. Med. 290: 1213-1216 (1974) (4 pages).

Lutgens et al. "Citrulline: a physiologic marker enabling quantitation and monitoring of epithelial radiation-induced small bowel damage." Int. J. Radiat Oncol. Biol. Phys. 57(4): 1067-1074 (2003) (8 pages).
Lutgens et al. "Plasma citrulline concentration: a surrogate end point for radiation-induced mucosal atrophy of the small bowel. A feasibility study in 23 patients." Int. J. Radiat. Oncol. Biol. Phys. 60(1): 275-285 (2004) (11 pages).
Mal-tsev et al. "The individual prognosis of the gravity and of the outcome of acute radiation disease based on immunological indexes." Journal of Radiation Biology 46(2): 152-158 (2006) (7 pages).
O'Grady et al. "Altered expression of the p53-regulated proteins, p21Waf1/Clip1, MDM2, and Bax in ultraviolet-irradiated human skin." Hum. Pathol. 29(6): 559-564 (1998) (6 pages).
Reif et al. "Iron release from ferritin and lipid peroxidation by radiolytically generated reducing radicals." Arch. Biochem. Biophys. 264(1): 238-243 (1988) (6 pages).
Salter et al. "Biodosimetry tools supporting the recording of medical information during radiation casualty incidents." Health Physics Society, 481-488 (2004) (10 pages).
Sine et al. "Biodosimety Assessment Tool: a post exposure software application for management of radiation accidents." Military Medicine 166:2, 85-87 (2001) (3 pages).
Thweatt et al. "Isolation and characterization of gene sequences overexpressed in Werner syndrome fibroblasts during premature replicative senescence." Exp. Gerontol. 27, 433-440 (1992) (8 pages).
Tomassi et al. "Radiation effects on the paratid gland of mammals. Part 3: Behavior of enzyme activity after irradiation." Strahlentherapie 155(8): 570-573 (1979) (4 pages).
Torti et al. "Iron and ferritin in inflammation and cancer." Advances in Inorganic Biochemistry 10, 119-137 (1994) (19 pages).
Torti et al. "Regulation of ferritin genes and protein." Blood 99, 3505-3516 (Available online at http://bloodjournal.hematologylibrary.org/cgi/content/full/99/10/3505) (2002) (13 pages).
Torti et al. "The molecular cloning and characterization of murine ferritin heavy chain, a tumor necrosis factor-inducible gene." J. Biol. Chem. 263:5, 12638-12644 (1988) (7 pages).
Tukachinskii et al. "Cx-reactive protein in radiation sickness." Bulletin of Experimental Biology and Medicine 52:8, 48-52 (1961) (4 pages).
Van Den Brenk et al. "Serum amylase as a measure of salivary gland radiation damage. Hyperamylasaemia following fractionated exposure to 4 MV X rays delivered in high pressure oxygen, and effects of certain steroids on this response." Journal of Radiology 42:501, 688-700 (1969) (13 pages).
Wei et al. "Interleukin 1 induces ferritin heavy chain in human muscle cells." Biochem. Biophys. Res. Commun. 169(1): 289-296 (1990) (8 pages).
Wood et al. "Studies on the Cx-reactive protein. The effects of irradiation of rabbits on the acute phase protein system." Journal of Experimental Medicine 111, 601-609 (1960) (Available online at http://jem.rupress.org/cgi/content/abstract/111/5/601) (9 pages).

* cited by examiner p21 WAF1/CIP1

Salivary amylase

C-reactive protein

IL-6

A

*Biomarkers: CRP, amylase activity, neutrophils, lymphocytes, and ratio of neutrophils to lymphocytes.

Figure 20.

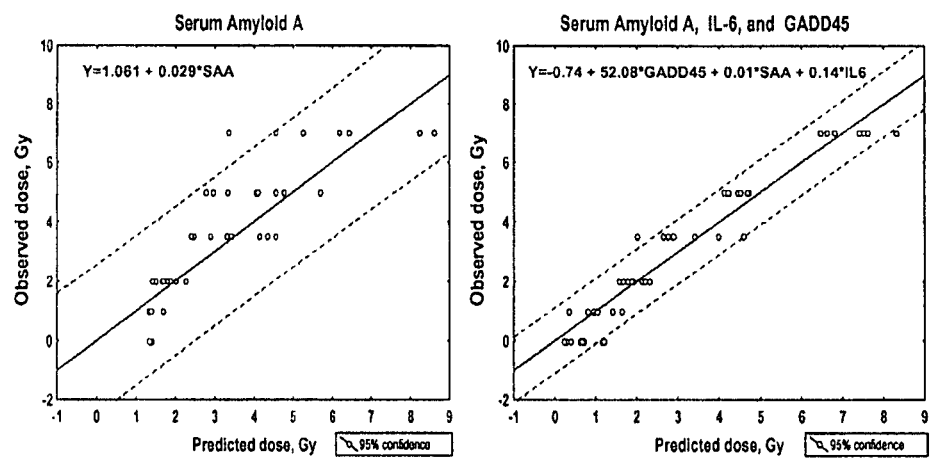

*In vivo* murine dose-response calibration curves for early-response exposure assessment using multiple radiation-responsive blood protein biomarkers $Y = a + b_1 * X_1 + b_2 * X_2 + ... + b_p * X_p$ where $Y$ is a dose assessment; $a$ is constant ; regression coefficients $b$ represent the independent contributions of each protein biomarker to the prediction of the dose; $X$ is a dose-response protein expression, $p$ is a number of protein biomarkers in the model.

BIOMARKER PANELS FOR ASSESSING RADIATION INJURY AND EXPOSURE

STATEMENT REGARDING FEDERALLY SPONSORED RESEARCH

Work described herein may have been supported in part by USUHS/AFRRI intramural protocol BD-10. The U.S. Government may have certain rights in the invention.

FIELD OF THE INVENTION

This application relates generally to the rapid assessment of radiation injury and radiation exposure and, in particular, to the use of a panel of two or more biomarkers for assessing radiation injury and radiation exposure.

BACKGROUND OF THE INVENTION

Current events throughout the world underscore the growing threat of different forms of terrorism, including radiological or nuclear attack. In the event of an attack, radiation exposures will be heterogeneous in terms of both dose and quality, depending on the type of device used and each victim's location relative to the radiation source. Acute effects of high-dose radiation include changes in peripheral blood cell numbers, immune suppression, mucosal damage (gastrointestinal and oral), and potential injury to other sites such as the bone marrow, lung, kidney and central nervous system (CNS). Long-term effects, as a result of both high- and low-dose radiation, include dysfunction or fibrosis in a wide range of organs and tissues and cancer. Early triage of suspected radiation over-exposed individuals is needed to determine individuals requiring immediate medical treatment.

One of the major tasks of first responders and medical personnel is to determine the internal and external radiation doses received by victims. This critical information provides diagnostic information to the treating physicians and provides exposure assessments for individuals at the site of the incident (such as first responders and medical staff). For example, hematological and blood chemistry bioindicators have been used in radiation exposure assessment (Blakely, 2005). Blood lymphocyte counts decline after radiation exposure in a dose dependent manner. In parallel, neutrophil (granulocyte) cell counts demonstrate an early rise followed by a steep decline following medically significant radiation exposure doses. Blakely and colleagues have developed radiation casualty software applications, including: Biodosimetry Assessment Tool (BAT) (Sine, 2001; Salter, 2004) and First-Responder Radiological Assessment Triage (FRAT), using MS Windows or Palm-based operating systems to support medical recording and triage. In the FRAT application, a multiple parameter triage feature permits an integrated and weighted assessment of these various biological exposure indicators.

The current methods used for estimating the radiation dose include time to emesis, lymphocyte depletion kinetics, cytogenetic changes, and location-based or physical dosimeter-based dose estimates. The currently available methodologies, however, are lacking the necessary quantitative indices to rapidly identify exposed individuals, as well as those who could benefit from immediate medical treatment.

Ionizing radiation elicits a number of detectable changes at the molecular, cellular and physiological level in exposed organisms. These biological parameters have been called biomarkers. Biomarkers of radiation exposure are biological parameters for which a dose-response relationship can be established and can be broadly referred to as biodosimeters. One such biodosimeter is the effect of ionizing radiation on expression patterns of proteins, as well as modifications in proteins.

The human genome has some 30,000 to 50,000 genes that represent the template for many more proteins, generally with proteomic patterns specific to cell types and tissues. Biological monitoring of molecular biomarkers can provide valuable radiation exposure assessment.

Radiation-responsive protein targets, typically measured in peripheral blood but in certain cases other body fluids (urine, saliva, etc.) are measured using immunoassays, including the conventional sandwich or variations of the enzyme-linked immunosorbent assay (ELISA), microsphere-based immunoassay (Luminex), lateral flow test strips, protein arrays, etc. However, as noted above, the measurement of any one radiation-responsive protein target alone does not provide the necessary quantitative indices to identify individuals exposed to radiation.

Hoffman and colleagues reported radiation-induced increases of serum salivary amylase in 41 patients, following either whole-body irradiation or irradiation of the head and neck region (Hoffmann, 1990). Becciolini and colleagues advocate the use of biochemical (e.g., serum salivary amylase and tissue polypeptide antigen) dosimetry for prolonged spaceflights (Becciolini, 2001). Bertho and colleagues irradiated non-human primates at doses ranging from 2 to 8 Gy, using whole-body or partial-body irradiation to assess a candidate plasma protein biomarker (Flt3-ligand) as an indicator of bone marrow damage for the management of accidental radiation-induced aplasia (Bertho, 2001). C-reactive protein (CRP) and other serum biomarkers, derived primarily from the liver, of acute phase reaction or inflammation have been proposed as radiation biodosimeters (Mal'tsev, 1978; Koc, 2003).

There remains a need in the art for a rapid means of assessing radiation injury and exposure in a patient, so that the most effective treatment can be provided to the subject. Although the prior art methods of measuring a single biomarker provide some information regarding a subject's exposure to radiation, the information provided is not sufficient to make an adequate diagnosis of the level of the subject's exposure. Furthermore, the information provided is not sufficient to help a clinician develop the best possible means of treatment for each subject individually and depending on their level of exposure.

SUMMARY OF THE INVENTION

The invention provides methods for assessing radiation injury and exposure in a subject comprising measuring the levels of at least two protein biomarkers in a test sample from the subject and correlating the levels of the at least two biomarkers with an assessment of radiation injury and exposure. In some embodiments, at least three protein biomarkers are measured, and in other embodiments, at least four protein biomarkers are measured.

The biomarkers can be from different biological pathways. For example, protein biomarkers such as salivary amylase, diamine oxidase, GADD45α, $p21^{Cip1/Waf1}$, p53, C-reactive protein, IL-6, Flt-3-ligand, TNF-α, alkaline phosphatase, Raf, Bax, Bcl-2, lipase, and citrulline can be measured in the methods of the invention.

In some embodiments of the invention, the at least two protein biomarkers can be C-reactive protein and salivary amylase, C-reactive protein and IL-6, or salivary amylase and IL-6. In other embodiments, the at least three protein biomarkers can be salivary amylase, C-reactive protein, and IL-6. In further embodiments, the at least four protein biomarkers can be p53, salivary amylase, C-reactive protein, and IL-6 or $p21^{Cip1/Waf1}$, salivary amylase, C-reactive protein, and IL-6.

The methods of the invention can be used on test samples from mammal subjects, such as human subjects. The test samples can be samples such as saliva, blood, plasma, serum, skin, and urine from the subject.

The levels of protein biomarkers can be measured with assays such as ELISA, microsphere-based immunoassays, lateral flow test strips, Western blots, and antibody-based dot blots. In some embodiments, the levels of protein biomarkers are measured at least 24 hours after suspected radiation exposure, and in some embodiments, the levels of protein biomarkers are measured at least 48 hours after suspected radiation exposure.

Another aspect of the invention provides methods for assessing radiation injury and exposure further comprising measuring at least one hematological parameter in a test sample. In these methods, the hematological parameter and the levels of at least two biomarkers are correlated with an assessment of radiation injury and exposure. The hematological parameter can be, for example, peripheral cell counts such as one or more of neutrophil levels, lymphocyte levels, platelet levels, and/or the ratio of neutrophil levels to lymphocyte levels. The hematological parameter can also be, for example, the level of Acute Phase Reaction biomarkers, such as C-reactive protein.

Another aspect of the invention provides methods for assessing radiation injury and exposure further comprising assessing physiological signs and symptoms exhibited by the subject. In these methods, the physiological signs and symptoms and the levels of at least two biomarkers are correlated with an assessment of radiation injury and exposure.

Yet another aspect of the invention provides methods for assessing the dose of radiation that the subject was exposed to. In these methods, the dose of radiation and the levels of at least two biomarkers are correlated with an assessment of radiation injury and exposure. The dose of radiation can be assessed by physical dosimetry-based estimates, including location-based estimates.

Yet a further aspect of the invention provides methods for assessing radiation injury and exposure in a subject comprising one or more of the steps of: measuring the levels of at least two protein biomarkers in a test sample from the subject, measuring at least one hematological parameter in the test sample, assessing physiological signs and symptoms exhibited by the subject, and assessing the dose of radiation that the subject was exposed to; and correlating one or more of: the levels of the at least two biomarkers, the at least one hematological parameter, the physiological signs and symptoms, and/or the dose of radiation that the subject was exposed to with an assessment of radiation injury and exposure.

Also provided by the invention are kits for assessing radiation injury and exposure comprising antibodies specific for at least two protein biomarkers and reagents for conducting an immunoassay. In some embodiments, the kits further comprise antibodies specific for a third protein biomarker, and in other embodiments, the kits further comprise antibodies specific for a fourth protein biomarker.

The kits can comprise reagents for conducting immunoassays, such as ELISA or microsphere-based immunoassays. The kits can further comprise reagents for lateral flow test strips. At least a portion of the antibodies for the protein biomarkers can be embedded in a lateral flow test strip.

In some embodiments, the kits can further comprise a device for measuring at least one hematological parameter, such as peripheral blood counts and/or Acute Phase Reaction biomarker levels. The device can be, for example, a fingerstick device. Peripheral blood counts can be one or more of neutrophil levels, lymphocyte levels, platelet levels, and/or the ratio of neutrophil levels to lymphocyte levels, and the Acute Phase Reaction biomarker can be C-reactive protein.

The various features of novelty which characterize the invention are pointed out with particularity in the claims annexed to and forming a part of this disclosure. For a better understanding of the invention, its advantages, and specific objects attained by its uses, reference is made to the accompanying drawings and descriptive matter in which preferred embodiments of the invention are illustrated.

BRIEF DESCRIPTION OF THE DRAWINGS

FIG. 20 shows multiple regression analysis used to develop dose-response relationships for multiple protein inductions for radiation dose assessment.

DETAILED DESCRIPTION OF THE INVENTION

Figure 1:
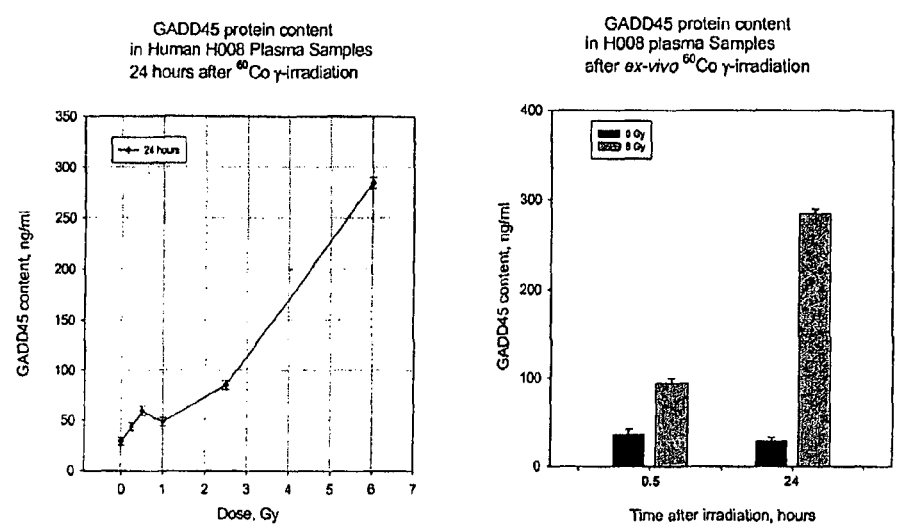
FIG. 1 shows radiation-responsive changes in the GADD45α levels in human blood cells at 24 hours after exposure to $^{60}Co$ gamma rays. Each symbol represents the mean of three independent experiments and error bars the standard error of means.
Figure 2:
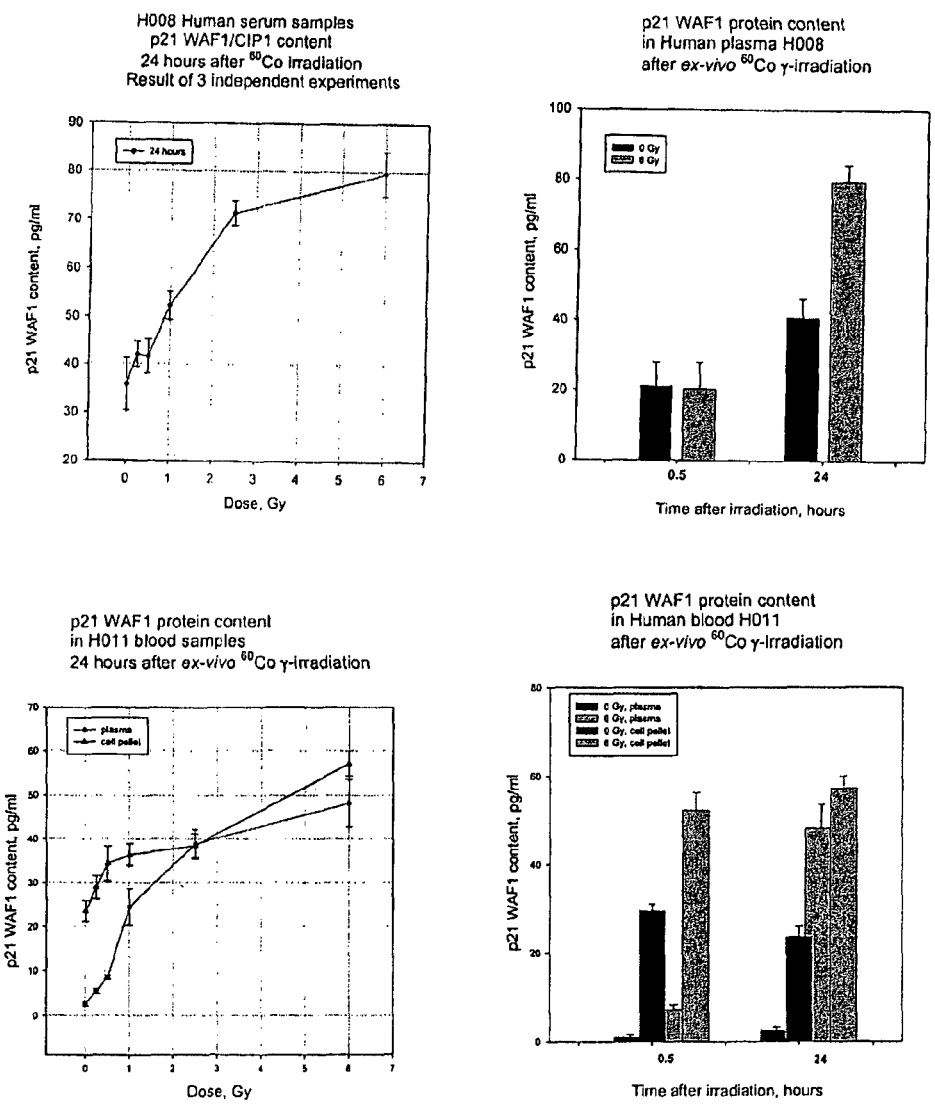
FIG. 2 shows radiation-responsive changes in the p21 WAF1 levels in human blood cells from two different donors at 24 hours after exposure to $^{60}Co$ gamma rays. Each symbol represents the mean of three independent experiments and error bars the standard error of means.
Figure 3:
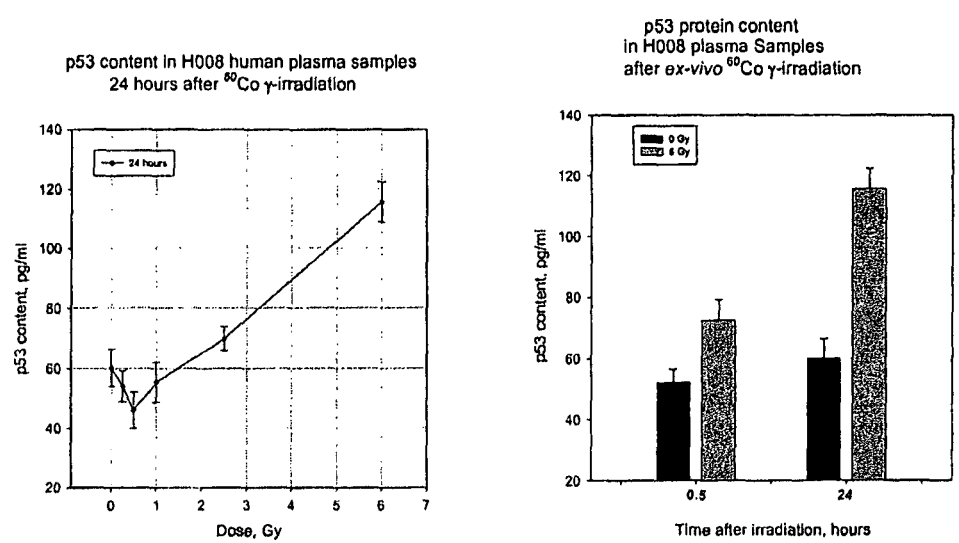
FIG. 3 shows radiation-responsive changes in the p53 levels in human blood cells at 24 hours after exposure to $^{60}Co$ gamma rays. Each symbol represents the mean of three independent experiments and error bars the standard error of means.
Figure 4:
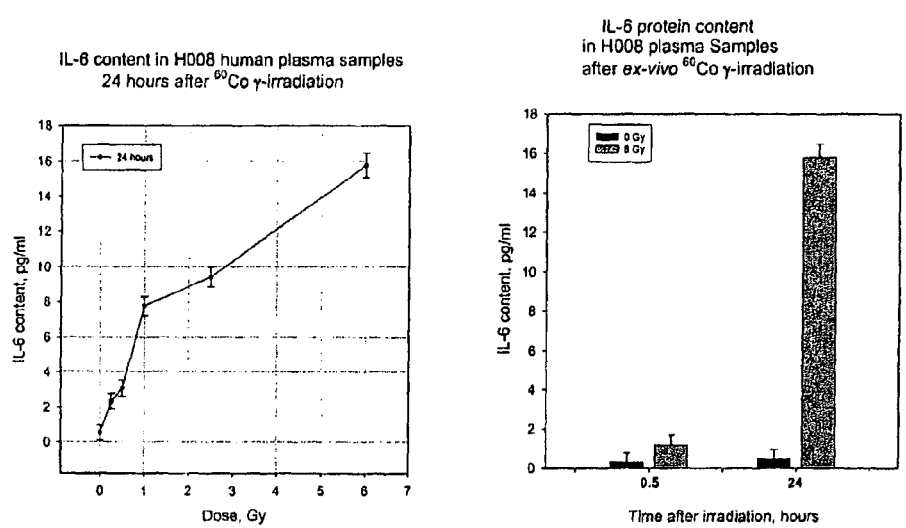
FIG. 4 shows radiation-responsive changes in the IL-6 levels in human blood cells at 24 hours after exposure to $^{60}Co$ gamma rays. Each symbol represents the mean of three independent experiments and error bars the standard error of means.
Figure 5:
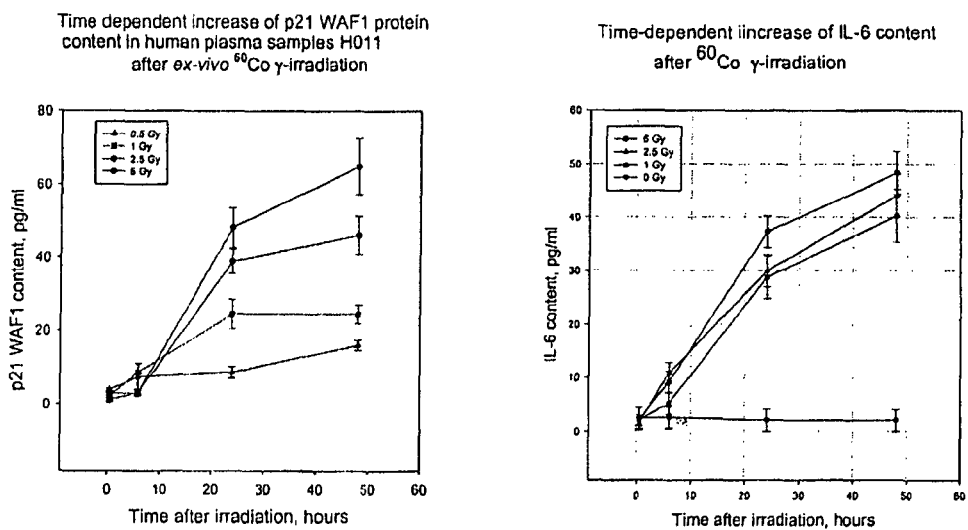
FIG. 5 shows dose and time dependent increases in p21 WAF1 and IL-6 protein content in human blood cells after exposure to $^{60}Co$ gamma rays.

For the purposes of promoting an understanding of the principles of the invention, reference will now be made to specific embodiment and specific language will be used to describe the same. It will nevertheless be understood that no limitation of the scope of the invention is thereby intended, such alteration and further modifications of the invention, and such further applications of the principles of the invention as illustrated herein, being contemplated as would normally occur to one skilled in the art to which the invention relates.

All terms as used herein are defined according to the ordinary meanings they have acquired in the art. Such definitions can be found in any technical dictionary or reference known to the skilled artisan, such as the *McGraw-Hill Dictionary of Scientific and Technical Terms* (McGraw-Hill, Inc.), *Molecular Cloning: A Laboratory Manual* (Cold Springs Harbor, N.Y.), *Remington's Pharmaceutical Sciences* (Mack Publishing, PA), and *Stedman's Medical Dictionary* (Williams and Wilkins, MD). These references, along with those references and patents cited herein are hereby incorporated by reference in their entirety.

Along with other diagnostic information indicative of radiation exposure (i.e., signs/symptoms, physical dosimetry based on personnel dosimeter or location, blood lymphocyte cell counts) the integrated results of levels for multiple protein targets (i.e. biomarkers) discriminates individuals with significant radiation exposure requiring immediate medical treatment. Efforts to establish and develop in vivo model systems to validate molecular biomarkers were pursued by the present inventors using radiation model systems involving three species (*Homo Sapiens, Mus musculus*, and *Macaca mulatta*).

The methods of the invention provide for assessment of radiation injury and exposure in a subject comprising measuring the levels of at least two (2) biomarkers and correlating the levels of the at least two biomarkers with an assessment of radiation injury and exposure. The methods of the invention can also comprise measuring the levels of at least three (3) biomarkers or at least four (4) biomarkers. The measurement of two or more biomarkers provides more detailed information regarding the extent of a subject's radiation injury/exposure than the prior art methods, which measured only one biomarker.

While there are many biomarkers that could be evaluated, the operational goal is to identify the minimum number of biomarkers that provide sufficient statistical robustness to effectively triage suspect radiation casualties for either follow-on more demanding diagnostic evaluation and/or early treatment decisions. Here data is provided showing that four protein biomarkers were 100% effective to discriminate 1-day irradiated from non-irradiated samples. Data is also provided showing that four protein biomarkers were 95% effective to discriminate 2-day irradiated from non-irradiated samples. In these cases, additional biomarkers do not provide added value.

Radiation exposure affects different pathways over periods of time. The dose and time dependency for the levels of blood protein biomarkers in humans is limited but suggest that some biomarkers are more sensitive to radiation exposure than others. Use of a non-human primate model affords an alternative in vivo radiation model to assess the levels of radiation-responsive blood protein biomarkers. Elevation of individual blood protein biomarkers are not uncommon and could be attributed to one of many non-radiation syndromes. A pattern showing elevation of one biomarker and not the other three tested from different radiation responsive pathways, would be considered to be inconsistent with significant whole-body radiation overexposures. Use of multiple protein biomarkers from different pathways present the basis for improved diagnostics of radiation injury and exposure assessment. This more detailed information provides the clinician more information regarding the extent of a subject's radiation exposure, and thus allows the clinician to make more appropriate treatment protocols on a patient by patient basis.

Biomarkers that can be measured in connection with the methods of the invention include, but are not limited to, salivary amylase, diamine oxidase, GADD45α, p21$^{Cip1/Waf1}$, p53, C-reactive protein, IL-6, Flt-3-ligand, TNF-α, alkaline phosphatase, Raf, Bax, Bcl-2, lipase, and citrulline. These radiation-responsive proteins are derived from tissues including: parotid gland, hematological tissues, intestine, liver, pancreas, nervous system, etc., as well as varied biological pathways including: DNA damage and repair, cell-cycle progression, cytokine, oncogenes, proteins along these biological pathways, or radiosensitive tissues can be used as biomarkers. Table 1 presents a selected list of radiation-responsive protein biomarkers and their respective tissue or cell location.

TABLE 1

| Proposed blood protein target | Target class | Tissue or cell location |
| --- | --- | --- |
| P53 | DNA damage and tumor suppression | Blood |

TABLE 1-continued

| Proposed blood protein target | Target class | Tissue or cell location |
|---|---|---|
| P21 WAF1/CIP1 | Cell cycle and cell proliferation | Blood |
| GADD45α | DNA damage and repair | Blood |
| Salivary α-Amylase | Tissue injury (enzyme) | Parotid glands |
| Cytokines (IL-6, Flt-3-ligand) | Immunomodulatory effects | Skin and blood |
| Acute-phase proteins (CRP, Serum Amyloid A, Ferritin) | Acute-phase reaction | Liver |

Radiation Responsive Protein Targets p53

P53 is a tumor suppressor protein that plays a major role in cellular response to DNA damage and other genomic aberrations. Activation of p53 can lead to either cell cycle arrest and DNA repair or apoptosis. After exposure to ionizing radiation p53 proteins accumulate in the nucleus and transactivate specific target genes. The p53 tumor suppressor is required for one such G1 checkpoint and functions to upregulate expression of GADD45α and p21.

p21 WAF1/CIP1

The cyclin-dependent kinase inhibitor p21 WAF1/CIP1, also known as wild-type p53-activated factor (WAF-1) and Cdk-interacting protein (CIP1), plays a critical role in cell differentiation. It also has been shown to confer resistance to apoptosis. P21 is induced by both p53-dependent and -independent mechanisms following stress. Induction of p21 may cause cell-cycle arrest. This expression usually is in response to DNA damage caused by ionizing radiation and cytotoxic agents. The expression of p21 interrupts the cell cycle and prevents the replication of cells containing genomic errors (Gartel, 2002; Bellido, 1998).

GADD45α

GADD45α (growth arrest and DNA damage inducible gene 45) is a multifunctional protein that is regulated by p53 and that may play a role in DNA replication and repair. There is evidence for its involvement in growth control, maintenance of genomic stability, cell cycle control, and apoptosis. GADD45α has been shown to interact with a number of proteins playing central roles in these cellular processes: such as proliferating cell nuclear antigen and p21 WAF1/CIP1.

Salivary α-Amylase

Apoptosis, or programmed cell death, can also occur after exposure to ionizing radiation. Some human cells are particularly sensitive to low levels of radiation. Once exposed to radiation, these cells exhibit activation of a signaling cascade that leads to DNA fragmentation and rapid cell death. Human cells that undergo radiation-induced apoptosis include lymphocytes and acinar cells of the salivary glands. Salivary α-amylase is a digestive enzyme secreted by salivary glands. The salivary glands in humans appear particularly radiosensitive and the effects of ionizing radiation can be evaluated by means of the determination of serum amylase. Elevations in serum amylase levels may occur within hours to days (Becciolini, 1980, 1984, 1987; Tomassi, 1979; Chen, 1973; Van Den Brenk, 1969). Patients submitted to external radiotherapy for tumors localized in the head and neck region show early and late effects on salivary glands. The modification of amylase activity appears as a progressive, statistically significant increase within two days. Levels of 200-300% of baseline values are reached, followed by a rapid return to pre-irradiation levels (Becciolini, 1980).

Cytokines (IL-6, Flt-3-Ligand)

Secreted by macrophages, the pro-inflammatory cytokine Interleukin 6 (IL-6) induces acute-phase reaction and plays an important role in immunity. Interleukin 6 (IL-6) is involved in p53-independent activation of p21 via different transcription factors (Gartel, 2002; Bellido, 1998). IL-6 is a chief stimulator of the production of most acute-phase proteins. IL-6 was shown to be an essential contributor for natural resistance to lethal irradiation. Expression of cytokines such as IL-6, IL-1, and TNFα as a result of inflammation through vascular and hematological damage is induced by radiation injury. The cytokines such as IL-6, TNF, and IL-1 may be useful to protect hematopoietic cells from radiation, while TNF may enhance the killing of tumor cells. Bertho and colleagues reported results for irradiated non-human primates at doses ranging from 2 to 8 Gy, using whole-body or partial-body irradiation to assess a candidate plasma protein biomarker Flt3-ligand as an indicator of bone marrow damage for the management of accidental radiation-induced aplasia (Bertho, 2001).

Acute-Phase Proteins CRP and SAA

The cytokines that are produced during and participate in inflammatory processes are the chief stimulators of the production of acute-phase proteins. The most notable acute-phase proteins synthesized by liver are C-reactive protein (CRP) and Serum Amyloid A (SAA).

CRP is a sensitive biomarker of disease with a broad clinical utility for cardiovascular injury monitoring and differential diagnosis. CRP plays an essential role in injuries caused by radiation (Wood, 1960; Tukachinski, 1961; Mal'tsev, 1978; Koc, 2003). Mal'tsev and colleagues reported data for CRP content in blood of 147 patients damaged at Chernobyl NPP accident as a result of radiation exposure. They determined that indexes of CRP content in a peripheral blood during primary reaction on the irradiation (1-2 days after) and in the latent period of radiation disease (3-9 days after) can provide the information for the prognosis of probable gravity (level) of radiation injury (Mal'tsev, 2006).

During acute events, the rise in the level of SAA in blood exhibits the most intense and rapid increase among all acute-phase proteins. Cytokines such as IL-1, IL-6, and TNF are considered mediators of SAA protein synthesis. Induction of serum amyloid A inflammatory response genes in bone marrow cell of mice exposed to total-body irradiation was reported by (Goltry, 1998). Significant elevation of serum amyloid A has been found in irradiated mice and cancer patients treated with a synthetic compound AS101 with radioprotective and chemoprotective effects (Kalechman, 1995).

Ferritin

Hematological biomarkers of exposure to ionizing radiation are well characterized and used in medical management of radiological casualties (Dainiak 2002). The combination of intestinal and hemopoietic syndromes results in dehydration, anemia, and infection, leading eventually to irreversible shock and death. Change in iron metabolism parameters (increased level of serum ferritin, appearance of an iron pool specifically unrelated to transferrin, reduced ceruloplasmin level, etc.) as affected by ionizing radiation were found changed in subjects who participated in liquidation of Chernobyl power plant accident aftereffects (Levina, 1993). The effect of iron release from ferritin using $^{137}Cs$ gamma radiation was investigated by Reif et al. (Reif, 1988). Observations over the last few years have placed the regulation of ferritin within the broad context of cell injury and stress as well as altered growth regulation (Torti, 2002).

Ferritin is a ubiquitous and highly conserved iron-binding protein. Ferritin also has enzymatic properties, converting Fe(II) to Fe(III) as iron is internalized and sequestered in the ferritin mineral core. Elemental iron is required for a variety of normal cellular functions. It is vital for proper growth and development. Iron is involved in the formation of oxidants capable of damaging membranes, protein, and DNA. Ferritin is a major protein involved in iron sequestration and detoxification. Increasingly, perturbations in cellular iron and ferritin are emerging as an important element in the pathogenesis of disease. These changes in ferritin are important not only in the classic diseases of iron acquisition, transport, and storage, such as primary hemochromatosis, but also in diseases characterized by inflammation, infection, injury, and repair.

The critical role of ferritin in cellular and organism iron homeostasis is intimately linked to its primary and best-studied function—iron sequestration. Iron in heme is necessary for the transport, binding, and release of oxygen; the ready availability of iron for incorporation to heme is essential to organism survival. Iron is also essential for the function of enzymes that participate in numerous critical cellular processes, including the cell cycle, the reductive conversion of ribonucleotides to deoxyribonucleotides, electron transport, and others.

One of the major functions of ferritin is to limit Fe(II) available to participate in the generation of oxygen-free-radicals (ROS). Oxidant stress is an ever-present threat to organism survival, both from exogenous and endogenous cellular sources; it is therefore not surprising that oxidant stress activates multiple pathways of ferritin regulation. Small quantities of ferritin are present in human serum, and are elevated in conditions of iron overload and inflammation (Lipschitz, 1974; Koziol, 2001; Torti, 1994).

Secretion of ferritin is stimulated by cytokines. Cytokines play a pivotal role in the cellular response to infection, and ferritin plays a prominent role in the cytokine response. TNFα, and interleukin 1α (IL-1α), another proinflammatory cytokine, transcriptionally induce the H chain of ferritin, suggesting that pathways related to inflammation and stress can impact on ferritin regulation (Torti, 1988; Wei, 1990).

Cytokines also have transcriptional effects on ferritin in different cell types. Ferritin induction in macrophages may be particularly important, given their central role in iron homeostasis as scavengers of old and damaged red blood cells, a critical and quantitatively important element in whole-body iron turnover. Cytokines also regulate ferritin posttranscriptionally: induction of ferritin synthesis was observed with a number of cytokines: IL-1β, IL-6, TNFα.

In some cell types, ferritin has been observed to increase in growth arrest (Larsson, 1998). Growth suppression associated with overexpression of ferritin H has also been reported (Cozzi, 2000). Upregulation of ferritin was also associated with induction of differentiation and growth arrest in hematopoetic systems (Thweatt, 1992).

Citrulline

Citrulline is an α-amino acid that is produced as an intermediate in the conversion of ornithine to arginine during urea formation in the liver. It is also produced from arginine as a by-product of the reaction catalyzed by nitric oxide synthase. Plasma citrulline has been found to be an effective protein marker for quantitation and monitoring of epithelial radiation-induced small bowel damage (Lutgens, 2003; Lutgens, 2004).

The biological samples which can be obtained from a subject and used for the methods of the invention include, but are not limited to, blood, plasma, serum, saliva, skin, urine, hair follicles, and other accessible tissues. The choice of biological sample used can depend on the biomarker that will be measured. For example, tissue from the parotid gland is used to measure salivary amylase activity, however, radiation issue is known to cause proteins from the parotid gland to be released in peripheral blood and then detected as an indicator of radiation overexposure (Becciolini, 2001). Skin tissue can be used to measure cytokine levels (IL-6, Flt-3-ligand, TNF-α, etc.). Blood can also be used to measure cytokine levels, as well as alkaline phosphatase, GADD45α and $p21^{Cip1/Waf1}$ levels. Liver tissue can be used to measure C-reactive protein (CRP) but as in the case of amylase above, following radiation exposure blood plasma levels of CRP are significantly elevated at one and two days after 6.5-Gy radiation exposure in non-human primate (*Macacq mulatta*) whole-body radiation models.

The use of hematological and serum enzyme activity biomarkers, evaluated in the early time frame after a suspected radiation exposure, in combination with the use of integrated multiple parameter triage tools can enhance radiation exposure discrimination and assessment. Examples of hematological parameters that can be evaluated include peripheral cell counts and/or Acute Phase Reaction biomarker levels. Peripheral cell counts include, for example, peripheral blood counts comprise one or more of neutrophil levels, lymphocyte levels, platelet levels, and/or the ratio of neutrophil levels to lymphocyte levels. Acute Phase Reaction biomarkers include, for example, C-reactive protein.

Accordingly, also provided by the invention are methods of assessing radiation injury and exposure in a subject comprising measuring the levels of at least two protein biomarkers and measuring at least one hematological parameter in a test sample and correlating the levels of the at least two protein biomarkers and the at least one hematological parameter with an assessment of radiation injury and exposure.

The invention further provides methods of assessing radiation injury and exposure in a subject comprising assessment of other diagnostic information indicative of radiation exposure. For example, in addition to hematological parameters, assessment of physiological signs and symptoms exhibited by the subject and an estimate of the dose of radiation that the subject was exposed to can be integrated with results of levels for multiple protein targets to improve the assessment of radiation injury and exposure. Physiological signs and symptoms that may be indicative of radiation exposure include signs and symptoms relating to the subject's neurovascular system (e.g. nausea, vomiting, anorexia, fatigue syndrome, fever, headache, hypotension, neurological deficits, cognitive deficits), hematopoietic system (e.g. lymphocyte changes, granulocyte changes, thrombocyte changes, blood loss, infection), cutaneous system (e.g. erythema, sensation/itching, swelling/edema, blistering, desquamation, ulcer/necrosis, hair loss, onycholysis), and/or gastrointestinal system (e.g. diarrhea, abdominal cramps/pain). An estimate of the dose of radiation that the subject was exposed to can be obtained, for example, by physical dosimetry based on personnel dosimeter or location-based estimates. Any method of assessing radiation injury and exposure comprising measuring the levels of at least two protein biomarkers combined with assessing one or more other diagnostic parameters indicative of radiation exposure is contemplated by the invention.

Assays and Kits for Measuring Protein Biomarkers

Methods for measuring the amount of biomarker present in a sample include, but are not limited to, ELISA, microsphere-based immunoassay, lateral flow test strips, antibody based dot blots or Westerns. Antibodies which can be used in any of these immunoassays include, but are not limited to, monoclonal or polyclonal antibodies to salivary amylase, IL-6, Flt-3 ligand, TNF-α, alkaline phosphatase, GADD45α, $p21^{Cip1/Waf1}$, C-reactive protein, Raf, Bax, Bcl-2, P53, lipase, etc. Chromatography (i.e., HPLC, GC, etc.) based separation and subsequent detection during various sensors (i.e., UV, fluorescence, etc.) as well as 2D-gel/matrix assisted laser desorption/ionization represents examples of alternative methods to measure protein levels for diagnostic radiation exposure assessment that does not require use of antibodies.

Also provided are kits for assessing radiation injury and exposure in a patient. Said kits comprise antibodies specific for a first biomarker; antibodies specific for a second biomarker; and reagents for conducting an immunoassay. The kits can further comprise antibodies for a third biomarker, and preferably will also comprise antibodies specific for a fourth biomarker. There can be more than one set of reagents present in the kit. For example, if the kit is intended for use with just ELISA, than only reagents for ELISA will be present. If the kit is intended for use with both ELISA and a microsphere-based immunoassay, then reagents for both ELISA and microsphere-based immunoassay will be present. If the kit is intended for use with ELISA, a microsphere-based immunoassay, and with lateral flow test strips, then reagents for all three immunoassays will be present, etc.

If lateral flow test strips are to be used to conduct the immunoassay, then the antibodies within the kit will be embedded in the lateral flow test strips. Also, the kits can be intended for use with a combination of immunoassays. So, for example, the antibodies for the first biomarker may be present in the kit as free antibodies, but a portion of them may also be embedded in a lateral flow test strip. The same can be said for the antibodies for the second biomarker, the third biomarker, and the fourth biomarker, etc.

The kits may include devices for measuring hematological parameters, such as peripheral blood counts and Acute Phase Reaction biomarkers. Such devices can be modifications of commercially available devices for assessing blood cell counts and APR biomarkers, such as the Quikread CRP finger-prick device (Orion Diagnostica, Finland) which measures the level of C-reactive protein.

Reference will now be made to specific examples illustrating the constructs and methods above. It is to be understood that the examples are provided to illustrate preferred embodiments and that no limitation to the scope of the invention is intended thereby.

EXAMPLES

Experimental protocols used to perform the studies that generated the data disclosed include a) radiation model systems and b) biomarker assays.

Radiation models employed include use of: a) human ex vivo radiation models, b) murine (*Mus musculus*) in vivo radiation models, and non-human primate (NHP) (*Macaca mulatta*) in vivo radiation models. In the human ex vivo radiation model, peripheral blood is drawn typically from healthy human donors, exposed ex vivo to ionizing radiation, and then incubated at 37° C. for various intervals. In the murine and NHP in vivo radiation models the animals are typically exposed to ionizing radiation and then blood is drawn at various times after exposure.

Biomarker assays employed include: a) protein assays based on ELISA and Luminex based methodology, b) enzyme assays (amylase activity) using a commercial based (BAYER) blood chemistry analyzer, and c) hematological cell counts using a commercial based (BAYER) hematology analyzer.

Example 1

Human Ex Vivo Radiation Model

Radiation responsive protein biomarkers were measured using ELISA and as well as a novel and high-throughput microsphere-based multi-analyte Luminex assay system. An in vitro model system of human peripheral blood lymphocytes showed radiation-responsive changes in the expression of GADD45α, p21 WAF1/CIP1, p53, and IL-6 with a progressive time- and dose-dependent increase (FIGS. 1-5). Protein levels were determined using a calibration curve with a reference standard. Symbols represent the mean of three independent experiments and error bars the standard error of means.

Figure 6:
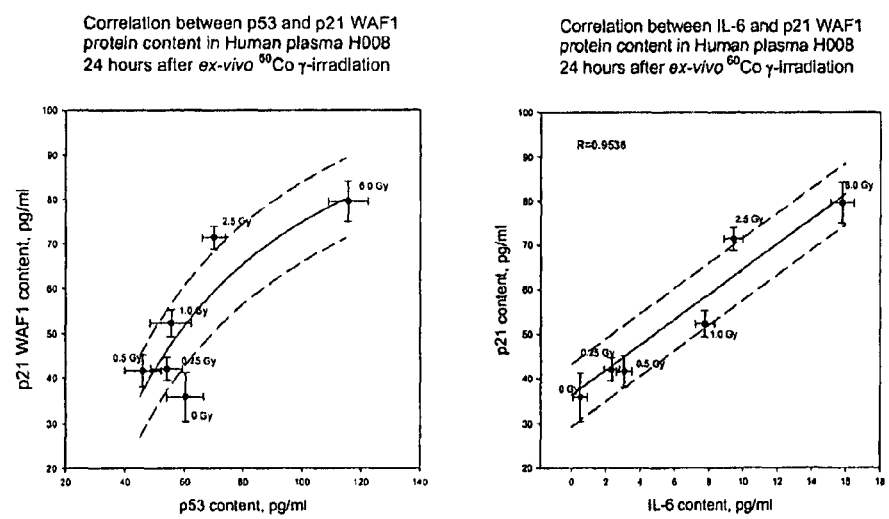
FIG. 6 shows correlations between p53, p21 WAF1, and IL-6 protein content in human blood cells at 24 hours after exposure to $^{60}Co$ gamma rays.
Figure 7:
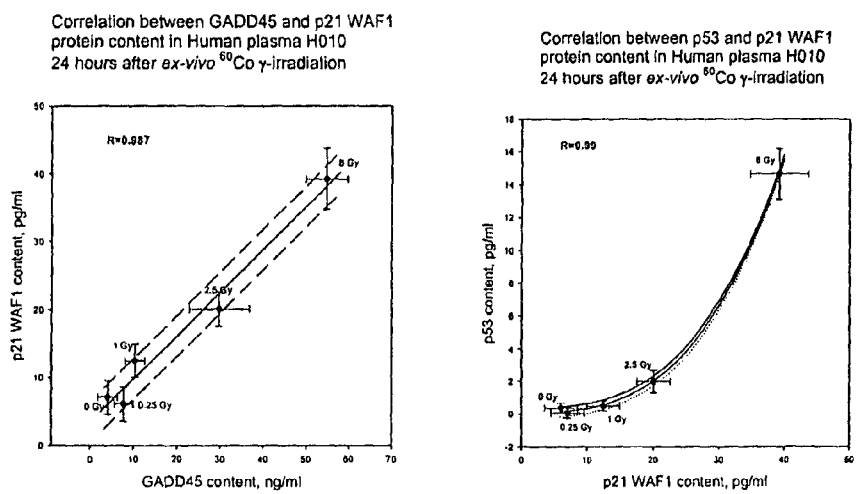
FIG. 7 shows correlations between p53, p21 WAF1, and GADD45α protein content in human blood cells at 24 hours after exposure to $^{6o}Co$ gamma rays.

Induction of these proteins by low-dose radiation has a different dependence on the time after irradiation than induction by high doses. Dose dependent increases in presented data show the potential utility of these protein biomarkers to detect radiation exposure. A retrospective correlation analysis led to the finding of strong correlations between different combinations of presented candidate radiation-responsive blood protein biomarkers (FIG. 6 and FIG. 7).

Example 2

Murine In Vivo Radiation Model

Figure 8:
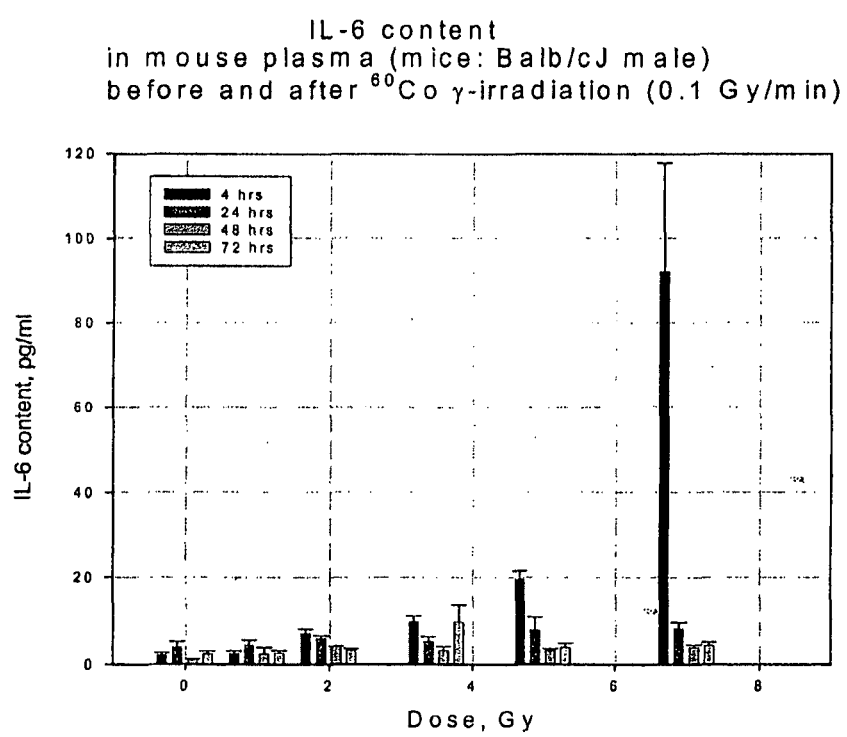
FIG. 8 shows IL-6 content in mouse plasma exposed to $^{60}Co$ gamma rays for a broad range of doses and time points.
Figure 9:
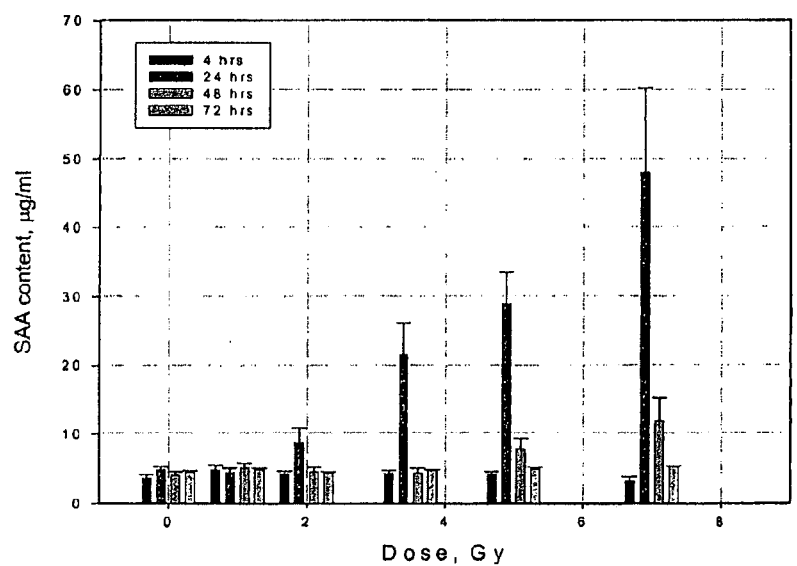
FIG. 9 shows serum amyloid A content in mouse plasma exposed to $^{60}Co$ gamma rays for a broad range of doses and time points.
Figure 10:
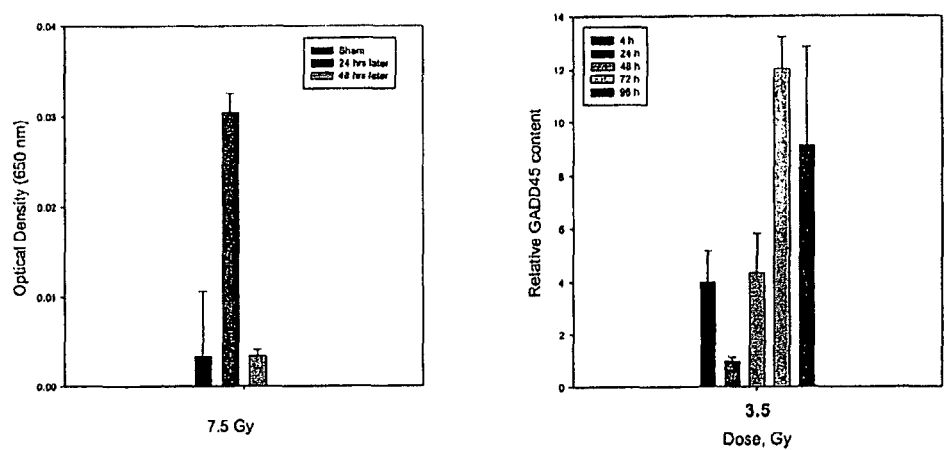
FIG. 10 shows ferritin and GADD45α protein content in mice plasma for selected irradiation doses of $^{60}Co$ gamma and sampling time points.

FIG. 8 shows the IL-6 content, and FIG. 9 shows the serum amyloid A content, in blood samples from mice exposed to Co-60 gamma rays at several sampling time-points. FIG. 10 shows results obtained using blood samples from mice exposed to Co-60 gamma rays for a broad dose range (0-7 Gy) and range of time points (6-96 hr).

Example 3

Non-Human Primate (Rhesus Macaques) In Vivo Radiation Model

Figure 11:
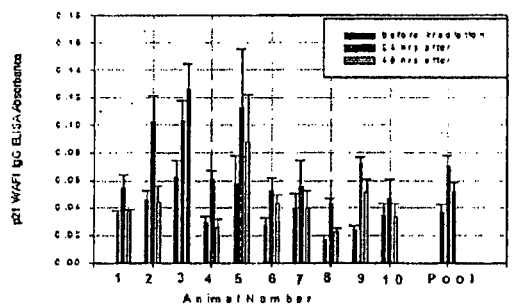
FIG. 11 shows radiation-responsive changes in the p21 WAF1, serum amylase, C-reactive protein, and IL-6 protein levels in monkey blood plasma samples at 24 and 48 hours after and before exposure to x-rays (6 Gy).
Figure 11:
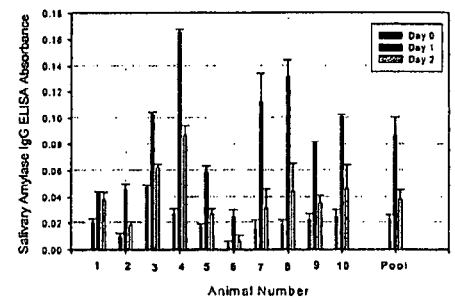
Figure 11:
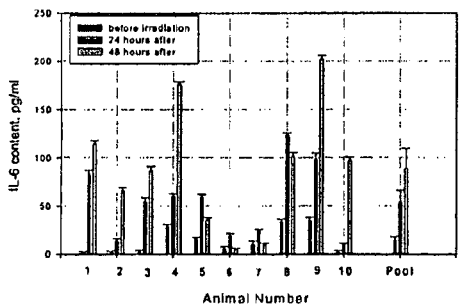
Figure 11:
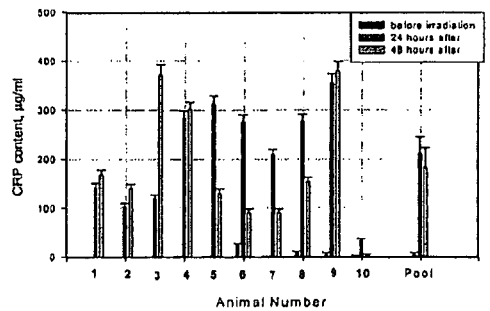

Blood samples from 10 rhesus monkeys exposed to 250 kVp x-rays (0.13 Gy/min) at several sampling time-points were obtained. FIG. 11 shows ELISA data (mean±SEM) for p21 WAF1/CIP1, salivary α-amylase, CRP, and IL-6 protein content measured immediately prior to 6-Gy whole-body irradiation and 24 and 48 h after exposure.

Figure 12:
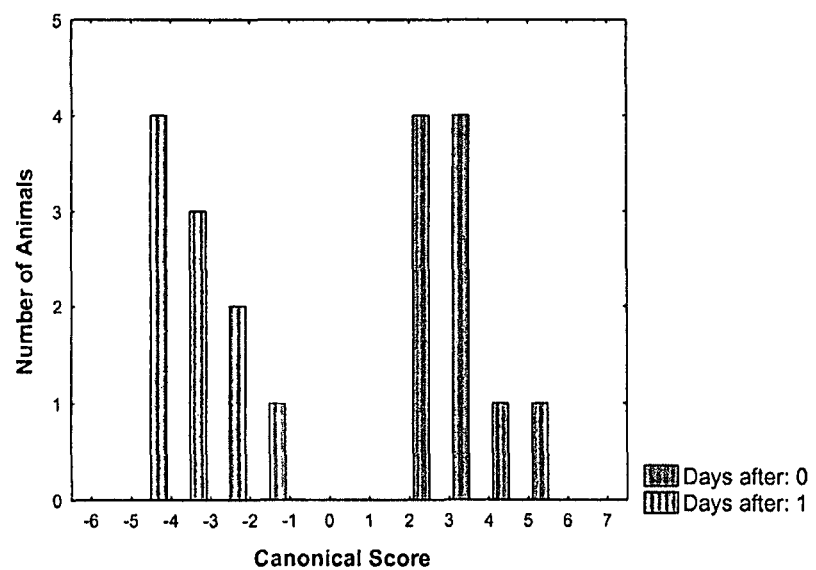
FIG. 12 shows discriminant analysis data for 4 biomarkers: p21 WAF1, serum amylase, C-reactive protein, and IL-6 from monkey samples: A) before and 1 day after, and B) before and 2 days after 6 Gy whole body x-ray irradiation. The results from (A) show 100% discrimination power and the results from (B) show 95% discrimination power.
Figure 12:
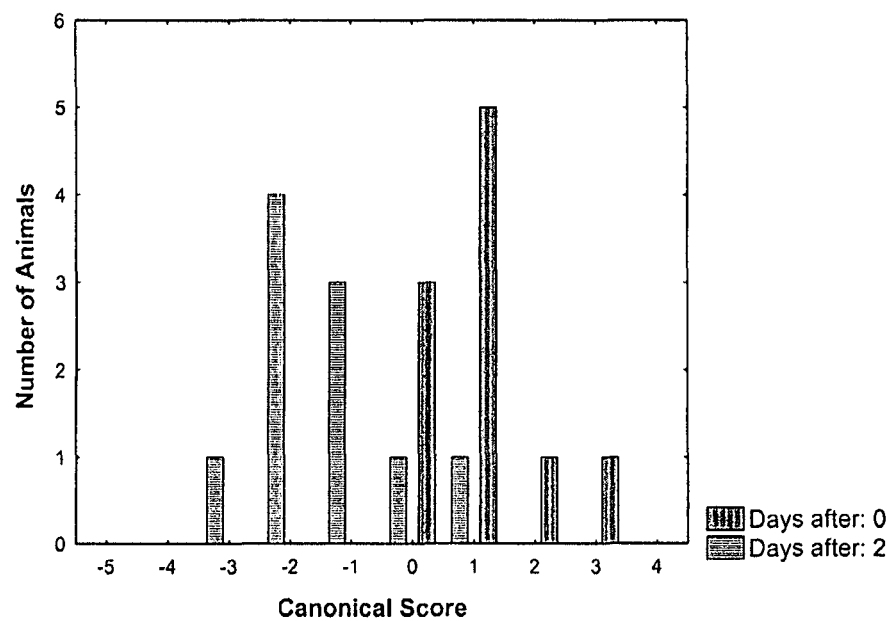
Figure 13:
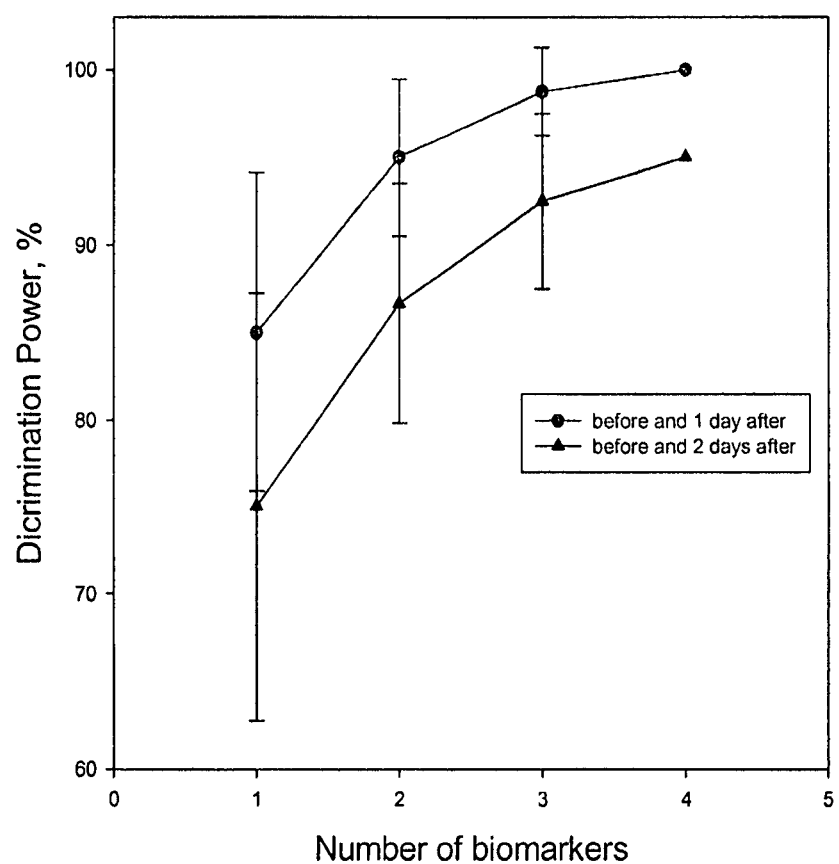
FIG. 13 shows discriminant analysis data for 1-4 biomarkers, representing different combinations of: p21 WAF1, serum amylase, C-reactive protein, and IL-6, from monkey samples before and 1 and 2 days after 6 Gy whole body x-ray irradiation. Progressive increases in the number of blood protein biomarkers from 1 to 4 provides increasing ability to discriminate irradiated from non-irradiated samples.

Data analyzed with use of multivariate discriminant analysis established very successful separation of non-human primate groups: 100% discrimination power for animals with correct classification for separation between groups before and 1 day after irradiation and 95% discrimination power for animals with correct classification for separation between groups before and 2 days after irradiation. (FIG. 12). Clear separation of animals before and after irradiation can be seen. The plot in FIG. 13 presents a result of classification and discrimination analyses for different combinations of biomarkers for 1 and 2 days after 6 Gy whole body irradiation. A progressive increase in the number of biomarkers from one to 4 improved the ability to discriminate control from exposed samples.

Multivariate discriminant analysis was performed using the Statistical Analysis Software (SAS) package to analyze the data for different combinations and number of measured biomarkers to separate monkey cohorts for different time points before and after 6-Gy whole-body irradiation. The DISCRIM procedure in SAS/STAT® calculates the posterior probability of each individual animal belonging to each of three subgroups (cohorts) and assigns the subject to a corresponding subgroup according to the higher probability. In addition, the DISCRIM procedure summarizes the squared distance between subgroups, univariate and multivariate statistics, canonical coefficients to derive canonical variables (a dimension-reduction technique), the list of misclassified observations, classification error-rate, the result of classification for each subject, and total frequency of separation. The purpose of the canonical score is to make separation between the classes as large as possible. Canonical scores represent the observation in the multidimensional space and can be positive or negative. Canonical scores have been used for 2D b-plots to aid the visual interpretation of group differences.

Materials and Methods

Model System, Radiation Exposure, and Peripheral Blood Biosampling

Domestic-born, male rhesus monkeys, *Macaca mulatta*, 4.8±0.7 kg, were housed in individual stainless steel cages in conventional holding rooms at the University of Maryland, Veterinary Resources Department in an animal facility accredited by the Association for the Assessment and Accreditation of Laboratory Animal Care International (AAALAC). Research was conducted according to the principles enunciated in the *Guide for the Care and Use of Laboratory Animals*, prepared by the Institute of Laboratory Animal Resources, National Research Council, and under an IACUC approved protocol. Rhesus monkeys received TBI to a midline tissue dose of 600 cGy, 250-kVp x-irradiation at 13 cGy min$^{-1}$. The dose (6 Gy) was selected to allow detection of a sufficient signal above background for whole-body exposure. Ketamine-anesthetized animals (Ketaset® [10 mg kg$^{-1}$, i.m.], Fort Dodge Laboratories; Fort Dodge, Ind.) were placed in a plexiglass restraint chair (to which they had been previously prehabituated), allowed to regain consciousness, and were x-irradiated in the posterior-anterior direction, then rotated at mid-dose to the anterior-posterior direction to complete the exposure. Dosimetry was performed using paired 0.5-cm$^3$ ionization chambers, with calibration factors traceable to the National Institute of Standards and Technology.

Blood sampling at pre-TBI and at 24 and 48 hours after were selected for this study based on radiation accident operational considerations. For example, generic guidelines recommend that blood for cytogenetic analysis be collected 24 hour after a suspect radiation exposure (IAEA, 2001). Tubes with collected peripheral blood were centrifuged at 800 g (4° C.) for 10 min to isolate the supernatant (plasma) and cell pellets. Blood samples were taken via aliquot and stored at −80° C. until use.

Protein Bioassays

Samples were assayed for colorimetric detection and quantitation of total protein via the bicinchoninic acid (BCA) method (Pierce) prior to the immunoassay. For ELISAs, plasma samples were diluted in phosphate-buffered saline (PBS) for equal amounts of 2.65 mg total protein content per each well. Polysterene 96-well microtiter plates (NUNC Brand Products, Nalge NUNC International, Rochester, N.Y.) were used to perform immunoassays.

The candidate radiation-responsive blood protein biomarker p21 WAF1/CIP1 was measured in newly developed modifications of indirect ELISA. Mouse monoclonal anti-p21 (Cat. #ab7903, Novus Biologicals, Inc., Littleton, Colo.) was added to plasma (antigen) passively adsorbed to a solid phase (96-well maxisorb polysterene plate). After 3 hours incubation at room temperature secondary antibody Biotin-SP-conjugated anti-mouse IgG (Cat. #115-065-003, Jackson Immuno-Research Laboratories, Inc., West Grove, Pa.) was added and incubated for 1 h at room temperature. After a wash step, horseradish peroxidase (HRP)-conjugated streptavidin (Streptavidin-HRP; R&D Systems, Inc., Minneapolis, Minn.) was added and incubated 20 min at room temperature. After a final wash step, the K-Blue substrate (Cat.#308176, Neogen Corporation, Lexington, Ky.) was added per manufacture guidance for color development. The reaction was stopped after 30 min using a stop solution (Cat.#301475, Neogen Corporation, Lexington, Ky.). The amount of color that developed was measured at 650 nm in a microtiter plate using a spectrophotometer (BIO-TEK Instruments, Inc., Winooski, Vt.). A human p21 WAF1 standard protein (Cat. #sc-4077 WB, Santa Cruz Biotechnology, Inc., Santa Cruz, Calif.) was used to check antibody responses.

Three replicate measurements per each of three independent experiments were determined for each sample. Data are presented as plasma p21 WAF1 IgG ELISA absorbance, which represents optical density (OD) units per equivalent total protein levels (2.65 mg) per well. The candidate radiation-responsive blood protein biomarker salivary α-amylase was measured in newly developed modifications of indirect ELISA. Rabbit polyclonal anti-alpha-amylase (Cat. #A36, Biomeda, Foster City, Calif.) was added to plasma (antigen) passively adsorbed to a solid phase (96-well maxisorb polysterene plate). After 3 hours, incubation at room temperature secondary-antibody-Biotin-SP-conjugated anti-rabbit IgG (Cat. #111-065-003, Jackson ImmunoResearch Laboratories, Inc., West Grove, Pa.) was added and incubated for 1 h at room temperature. After a wash step, horseradish peroxidase (HRP)-conjugated streptavidin (Streptavidin-HRP, R&D Systems, Inc., Minneapolis, Minn.) was added and incubated at room temperature. After a final wash step, the K-Blue substrate (Cat.#308176, Neogen Corporation, Lexington, Ky.) was added for color development. The reaction was stopped after 30 min using a stop solution (Cat.#301475, Neogen Corporation, Lexington, Ky.). The amount of color that developed was measured at 650 nm in a microtiter plate using a spectrophotometer. A human salivary α-amylase standard protein (Cat. #A1031, Sigma-Aldrich, St. Louis, Mo.) was used to check antibody responses.

Sandwich ELISA for monkey C-reactive protein (CRP) was performed using a commercially available kit (Cat. #2210-4, Life Diagnostics, Inc., West Chester, Pa.) according to the manufacturer's instructions. The sensitivity for assay was 0.8 ng ml$^{-1}$. Three replicate measurements were determined for each sample and standards.

A sandwich ELISA for monkey IL-6 was performed using a commercially available kit (Cat. #CKM005, Cell Sciences, Inc., Canton, Mass.). The sensitivity for assay was 1 pg ml$^{-1}$. Three replicate measurements were determined for each sample and standards.

The CRP and IL-6 concentrations in plasma samples were determined via use of Table Curve 2D software.

Data Analysis

Statistical software, PC SAS was used for statistical analyses (SAS Institute Inc., 2000; Khattree et al., 2000). Multivariate analysis of variance (MANOVA) was used to determine if there was a significant difference among three sampling time points in any outcome variable, by using Wilks' Lambda statistics. If there was a significant difference among the three days, then pairwise comparisons were used. A significance level was set at 5% for each test. All statistical tests were two-sided. Adjustment of multiple tests was not made. For each monkey at a given day, average of the three observations for an outcome variable was used for the statistical analyses. The DISCRIM procedure was used in data analysis to separate irradiated subgroup of animals from non-irradiated. Discriminant analysis is a multivariate statistical procedure that mathematically defines a special discriminant function to separate study animal groups by one classification variable (time after irradiation).

Results and Discussion

Exposure of non-human primates to 6 Gy x-rays resulted in the up-regulation of plasma levels of DNA-repair, cell-cycle inhibitor p21 WAF1/CIP1, the pro-inflammatory cytokine Interleukin 6, tissue enzyme salivary α-amylase, and acute-phase protein CRP synthesized by the liver.

p21 WAF1/CIP1

Plasma p21 WAF1/CIP1 protein content baseline values in rhesus monkeys ranged from 0.017 (±0.003) to 0.063 (+0.011) IgG ELISA absorbance with a pooled cohort mean value of 0.038 (±0.005); FIG. 11, upper left panel). In individual monkeys, radiation caused a 1.35- to 2.91-fold increase (pooled value of 1.95-fold) in plasma p21 WAF1 protein content at 24 h relative to the individual baseline values. The pooled value of plasma p21 WAF1 protein content in the cohort (n=10) was increased by 1.95- and 1.34-fold at 24- or 48-h, respectively, after radiation. P21 WAF1 levels at baseline increased at 24-h and then decreased at 48-h significantly, while the levels at 48-h increased from the baseline not significantly ($p=0.0001, 0.0158, 0.0679$ respectively; MANOVA $p=0.0009$).

Salivary α-Amylase

Plasma salivary α-amylase protein content baseline values in monkey samples ranged from 0.010 (±0.003) to 0.085 (±0.007) IgG ELISA absorbance with a pooled cohort mean value of 0.021 (±0.004); FIG. 11, upper right panel). In individual monkeys, radiation caused a 2.15- to 7.03-fold increase (pooled value of 4.48-fold) in plasma salivary α-amylase protein content at 24 h relative to individual baseline values. The pooled value of plasma p21 WAF1 protein content in the cohort (n=10) was increased by 4.48- and 1.91-fold at 24 or 48 h, respectively, after radiation. Salivary protein levels at baseline increased at 24-h and then decreased at 48-h significantly, and the levels at 48-h significantly increased from the baseline ($p=0.0005, 0.0043, 0.0005$ respectively; MANOVA $p=0.0034$).

C-Reactive Protein

The lower left panel of FIG. 11 shows measurement results of CRP protein expression in monkey plasma. Significantly increased plasma CRP levels are observed at 24 and 48 h post irradiation. Plasma CRP content baseline values ranged from 0.37 (±0.10) ug ml$^{-1}$ to 24.21 (±1.88) ug ml$^{-1}$ with a pooled cohort mean value of 4.90 (±2.34) ug ml$^{-1}$. In individual monkeys, radiation caused an 11.15- to 341.07-fold increase (pooled value of 210.28-fold) in plasma CRP content at 24 h relative to individual baseline values. The pooled value of plasma CRP content in the cohort (n=10) was increased by 210.28- and 182.22-fold at 24 or 48 h, respectively, after radiation. CRP levels at baseline significantly increased at 24-h and then decreased at 48-h not significantly, while the levels at 48-h significantly increased from the baseline ($p=0.0001, 0.5180, 0.0017$ respectively; MANOVA $p=0.0008$).

Interleukin 6 (IL-6)

The lower right panel of FIG. 11 shows the result of measuring IL-6 expression in monkey plasma. One can see significantly increased plasma IL-6 levels at 24 and 48 h post irradiation. Plasma IL-6 content baseline values ranged from 1.15 (±1.09) pg ml$^{-1}$ to 35.48 (±2.38) pg ml$^{-1}$ with a pooled cohort mean value of 13.34 (±4.45) pg ml$^{-1}$. In individual monkeys, radiation caused a 2.11- to 72.44-fold increase (pooled value of 13.75-fold) in plasma CRP content at 24 h relative to the individual baseline values. The pooled value of plasma CRP content in the cohort (n=10) was increased by 13.75- and 27.37-fold at 24 or 48 h, respectively, after radiation. IL-6 levels at baseline increased at 24-h significantly and then increased at 48-h not significantly, while the levels at 48-h significantly increased from the baseline ($p=0.0021, 0.0648, 0.0025$ respectively; MANOVA $p=0.0047$).

Data presented show the potential utility of protein biomarkers to detect radiation exposure. The DISCRIM procedure in SAS/STAT® was used in data analysis by the definition a special discriminant function to separate study animal groups by one classification variable (time after irradiation). The discriminant function can use several quantitative variables (biomarkers), each of them makes an independent contribution to the overall discrimination. Taking into consideration the effect of all quantitative variables, this discriminant function produces the statistical decision for guessing to which subgroup of classification variable each subject (animal) belongs to. The DISCRIM procedure in SAS/STAT® calculates the posterior probability of each individual animal belonging to each of three subgroups and assigns the subject to a corresponding subgroup according to the higher probability; summarizes the squared distance between subgroups in multidimensional (dimension is a number of independent variables) space taking into account correlations between variables. The DISCRIM procedure produces quantitative variables: Wilks' Lambda that assume values in the range of 0 (perfect discrimination) to 1 (no discrimination) and provides information about upper limit for number of biomarkers and Partial Lambda associated with the unique contribution of the respective variable (biomarker) to the discriminatory power of the model. Procedure derives a list of misclassified observations, classification error-rate, the result of classification for each subject, and canonical scores that represent the observation in the multidimensional space. Canonical scores have been used for 2D-plots to aid the visual interpretation of subgroup differences. The purpose of the canonical score is to make separation between the classes as large as possible. Thus, when observations are plotted with canonical scores as the coordinated, observations belonging to the same class are grouped together. As a result of classification and discrimination analysis, we also have a list with detailed information for each animal: predicted and observed classification.

FIGS. 12 and 13 show the results of discriminant analysis for different combinations and a number of biomarkers for 24 and 48 h after 6-Gy whole-body irradiation. Error bars represent the standard deviation for discrimination power values for a given number of biomarkers. An enhanced separation between animal groups was observed as the number of biomarkers increased. FIG. 12 shows separation of animals before and 24 h and 48 h after 6-Gy whole-body irradiation for four protein biomarkers: p21 WAF1/CIP1, salivary α-amylase, CRP, and IL-6. Results demonstrate a distinct separation of animals with 100% discrimination power (without any overlap) between before and 24 h after irradiation.

Example 4

Non-Human Primate (Rhesus Macaques) In Vivo Radiation Model

Figure 14:
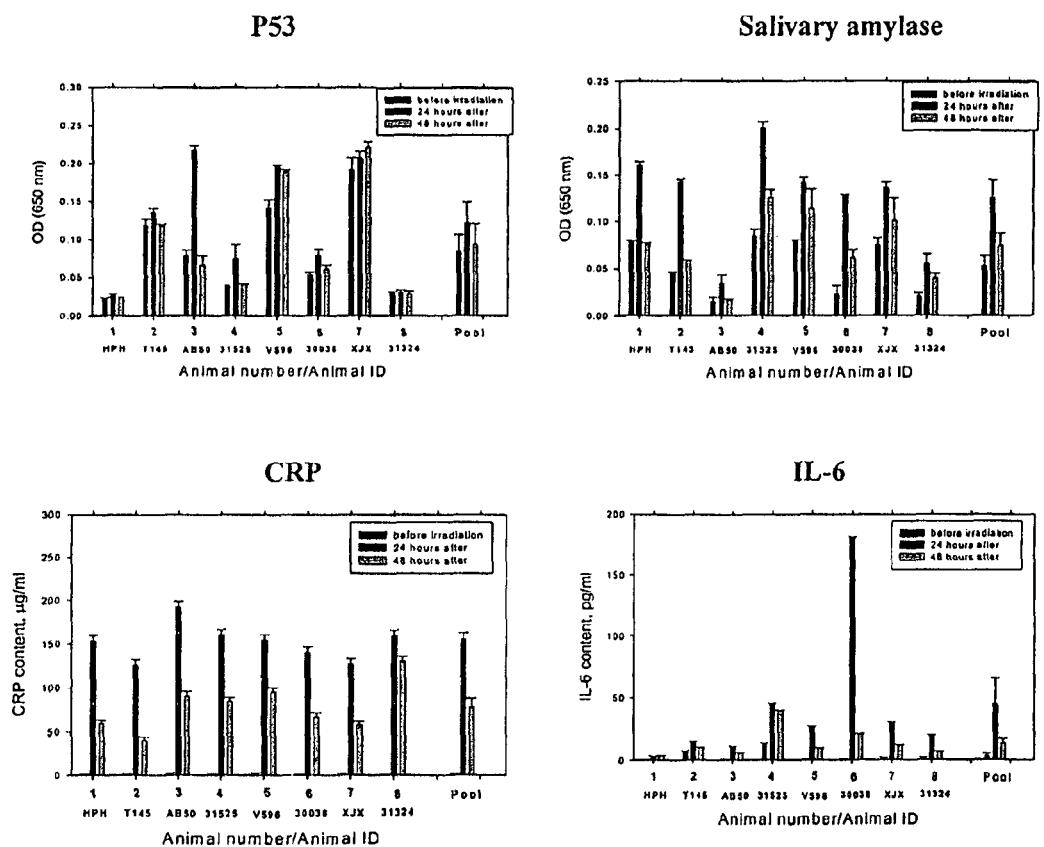
FIG. 14 shows radiation-responsive changes in the p53, serum amylase, C-reactive protein, and IL-6 protein levels in monkey samples at 24 and 48 hours after and before exposure to $^{60}$Co gamma rays (6.5 Gy).

Blood samples from 8 rhesus monkeys exposed to 6.5 Gy $^{60}$Co gamma-rays (0.4 Gy/min) at several sampling time-points were obtained. FIG. 14 shows ELISA data (mean±SEM) for p53, salivary α-amylase, CRP, and IL-6 protein content measured immediately prior to 6.5-Gy whole-body irradiation and 24 and 48 h after exposure.

Figure 15:
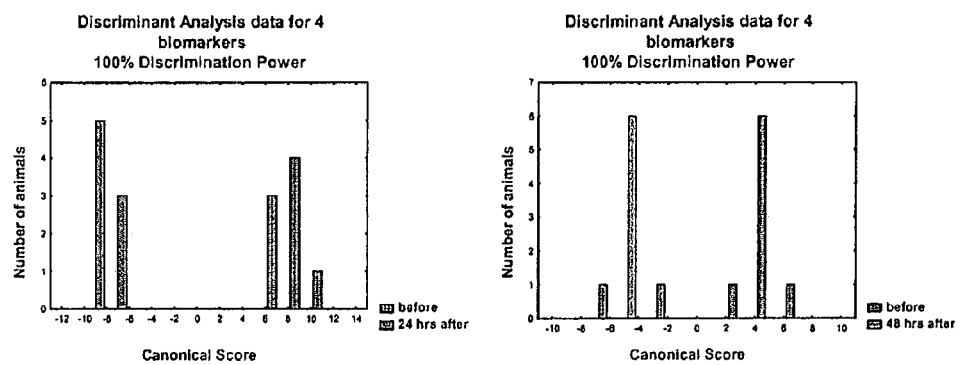
FIG. 15 shows discriminant analysis data for 4 biomarkers: p53, serum amylase, C-reactive protein, and IL-6 from monkey samples: A) before and 1 day after, and B) before and 2 days after 6.5 Gy whole body gamma irradiation. The results from both (A) and (B) show 100% discrimination power.
Figure 16:
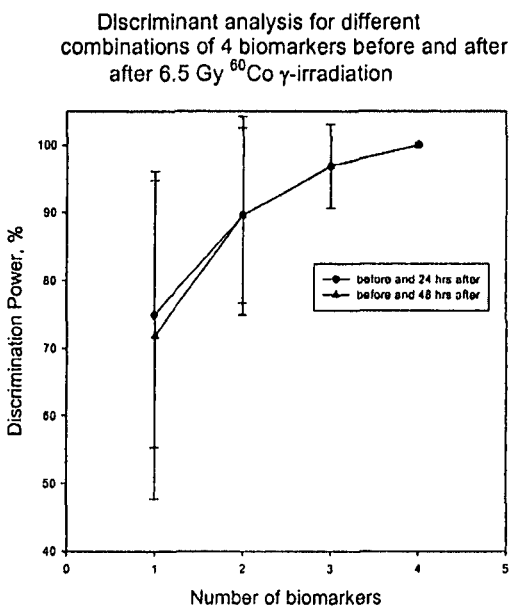
FIG. 16 shows discriminant analysis data for 1-4 biomarkers, representing different combinations of: p53, serum amylase, C-reactive protein, and IL-6, from monkey samples before and 1 and 2 days after 6.5 Gy whole body gamma irradiation.

Data analyzed with use of multivariate discriminant analysis established very successful separation of non-human primates groups: 100% discrimination power for animals with correct classification for separation between groups before and after irradiation (FIG. 15). Clear separation of animals before and after irradiation can be seen. The plot in FIG. 16 presents a result of classification and discrimination analyses for different combinations of biomarkers for 1 and 2 days after whole body irradiation. A progressive increase in the number of biomarkers from one to 4 improved the ability to discriminate control from exposed samples.

Example 5

Amylase and Blood Cell-Count Hematological Radiation-Injury Biomarkers in a Rhesus Monkey Radiation Model—Use of Multiparameter and Integrated Biological Dosimetry We investigated the utility of serum amylase and hematological blood-cell count biomarkers to provide early assessment of severe radiation exposures in a non-human primate model (i.e., rhesus macaques; n=8) exposed to whole-body radiation of $^{60}$Co-gamma rays (6.5 Gy, 40 cGy min$^{-1}$). Serum amylase activity was significantly elevated (12.3±3.27- and 2.6±0.058-fold of day zero samples) at 1 day and 2-days, respectively, after radiation. Lymphocyte cell counts decreased (≤15% of day zero samples) 1 and 2 days after radiation exposure. Neutrophil cell counts increased at day one by 1.9(±0.38)-fold compared with levels before irradiation. The ratios of neutrophil to lymphocyte cell counts increased by 13(±2.66)- and 4.23(±0.95)-fold at 1 and 2 days, respectively, after irradiation. These results demonstrate that increases in serum amylase activity along with decreases of lymphocyte counts, increases in neutrophil cell counts, and increases in the ratio of neutrophil to lymphocyte counts 1 day after irradiation can provide enhanced early triage discrimination of individuals with severe radiation exposure and injury.

Materials and Methods

Model System, Radiation Exposure, and Peripheral Blood Biosampling

Male rhesus monkeys (*Macaca mulatta*) (6.8 to 12.2 kg; 7 to 10 y old; n=8), were housed in individual stainless steel cages in conventional holding rooms at the AFRRI's Veterinary Sciences Department in an animal facility accredited by the Association for Assessment and Accreditation of Laboratory Animal Care (AAALAC) International. Research was conducted according to the principles enunciated in the *Guide for the Care and Use of Laboratory Animals*, prepared by the Institute of Laboratory Animal Resources, National Research Council.

Rhesus monkeys received myeloablative conditioning as total-body exposure to a midline tissue dose of 6.50 Gy, $^{60}$Co-γ irradiation at 40 cGy m$^{-1}$. The dose (6.5 Gy) was selected as part of a medical countermeasures study. Ketamine-anesthetized animals (Ketaset® [10 mg kg$^{-1}$, i.m.], Fort Dodge Laboratories; Fort Dodge, Ind.) were placed in a plexiglass restraint chair (to which they had been previously habituated), allowed to regain consciousness and were irradiated bi-laterally. Dosimetry was performed using an alanine/electron paramagnetic respondance system, with calibration factors traceable to the National Institute of Standards and Technology and confirmed by an additional check against the national standard $^{60}$Co source of the UK National Physics Laboratory.

Approximately 1-2 h prior to irradiation and then 24- and 48-h after irradiation, peripheral blood (≤1.5×10$^{-3}$ l) was drawn from ketamine-anesthetized animals by saphenous vein into either a serum separator (Cat.#365967, Becton Dickinson and Company, Franklin Lakes, N.J.) and potassium EDTA (Cat.#365974, Becton Dickinson) vacutainer tubes. Blood in EDTA tubes for white blood cell count measurements were analyzed within several h after biosampling. Blood collected into serum separator tubes for amylase activity were centrifuged at 800 g (4° C.), and stored at 4° C. prior to analysis <3 days. EDTA tubes for ELISA-based amylase protein measurements were centrifuged at 800 g (4° C.) for 10 min to isolate the supernatant (plasma) and cell pellet. Blood plasma samples were aliquoted and stored at −80° C. for analysis of α-amylase protein content.

Peripheral Blood Cell Counts

Complete blood cell counts and differentials were determined using a clinical hematology analyzer (Bayer Advia 120, Bayer, Tarrytown, N.Y.). Three replicate measurements were performed for each sample.

Serum Amylase Activity

Amylase activities from serum samples were measured using a clinical blood chemistry analyzer (Bayer Vitros 250, Ortho-Clinical Diagnostics, Rochester, N.Y.). Preliminary analysis determined that the samples from irradiated animals were elevated and required 10-fold dilutions for measurements to fall within the calibrated dose range. Three replicate measurements were determined for each sample.

Plasma α-Amylase

The candidate radiation-responsive blood protein biomarker, salivary α-amylase, was measured in a modification of an enzyme-linked immunosorbent assay (ELISA). Samples are assayed for colorimetric detection and quantitation of total protein via the bicinchoninic acid (BCA) method (Pierce) prior to the immunoassay. For ELISA, plasma samples were diluted in phosphate buffered saline (PBS) to yield an equal amount (2.65 mg) of total protein content per each well (100 µl). Polysterene 96-well microtiter plates (Nalge NUNC International, Rochester, N.Y.) were used to perform immunoassays.

Rabbit polyclonal α-amylase antibody (Cat. #A36, Biomeda, Calif.) was added to plasma (antigen) passively adsorbed to a solid phase (96-well maxisorb polysterene plate). After 3 h incubation on a shaker at room temperature, secondary Ab:Biotin-SP-conjugated AffiniPure Goat anti-rabbit IgG (Cat. #111-065-003, Jackson ImmunoResearch Laboratories, Inc., West Groove, Pa.) antibody was added and incubated for 1 h at room temperature. After a wash step, horseradish peroxidase (HRP)-conjugated streptavidin (Streptavidin-HRP) (R&D Systems, Inc., Minneapolis, Minn.) was added (100 µl; 1:200 dilution) and incubated 20 min at room temperature. After a final wash, the substrate (Neogen Corporation, Lexington, Ky.) 100 µl was added for color development. The reaction was stopped after 30 min with 50 µl of stop solution (Neogen Corporation). The amount of color that developed was measured at 650 nm in the microtiter plate using a spectrophotometer (BIO-TEK Instruments, Inc., Winooski, Vt.). Human salivary amylase standard protein (Cat. #A1031, Sigma-Aldrich, Saint Louis, Mo.) was used to check antibodies' response. Three replicate measurements were determined for each sample. Data are presented as plasma amylase IgG ELISA absorbance, representing OD units per equivalent total protein levels (2.65 mg) per well.

Data Analysis

Multivariate analysis of variance (MANOVA) repeated measures analysis was used to determine if there was a significant difference among day 0, day 1, and day 2 in any outcome variable, by using the Wilks' Lambda statistics. If there was a significant difference among the three days, then we compared day 1 and day 2 results versus day 0, respectively (Morrison, 1976). A significance level was set at 5% for each test. All statistical tests were two-sided. A statistical software package (Personal Computer-Statistical Analysis Software) was used for statistical analyses.

Results

Hematology

Figure 17:
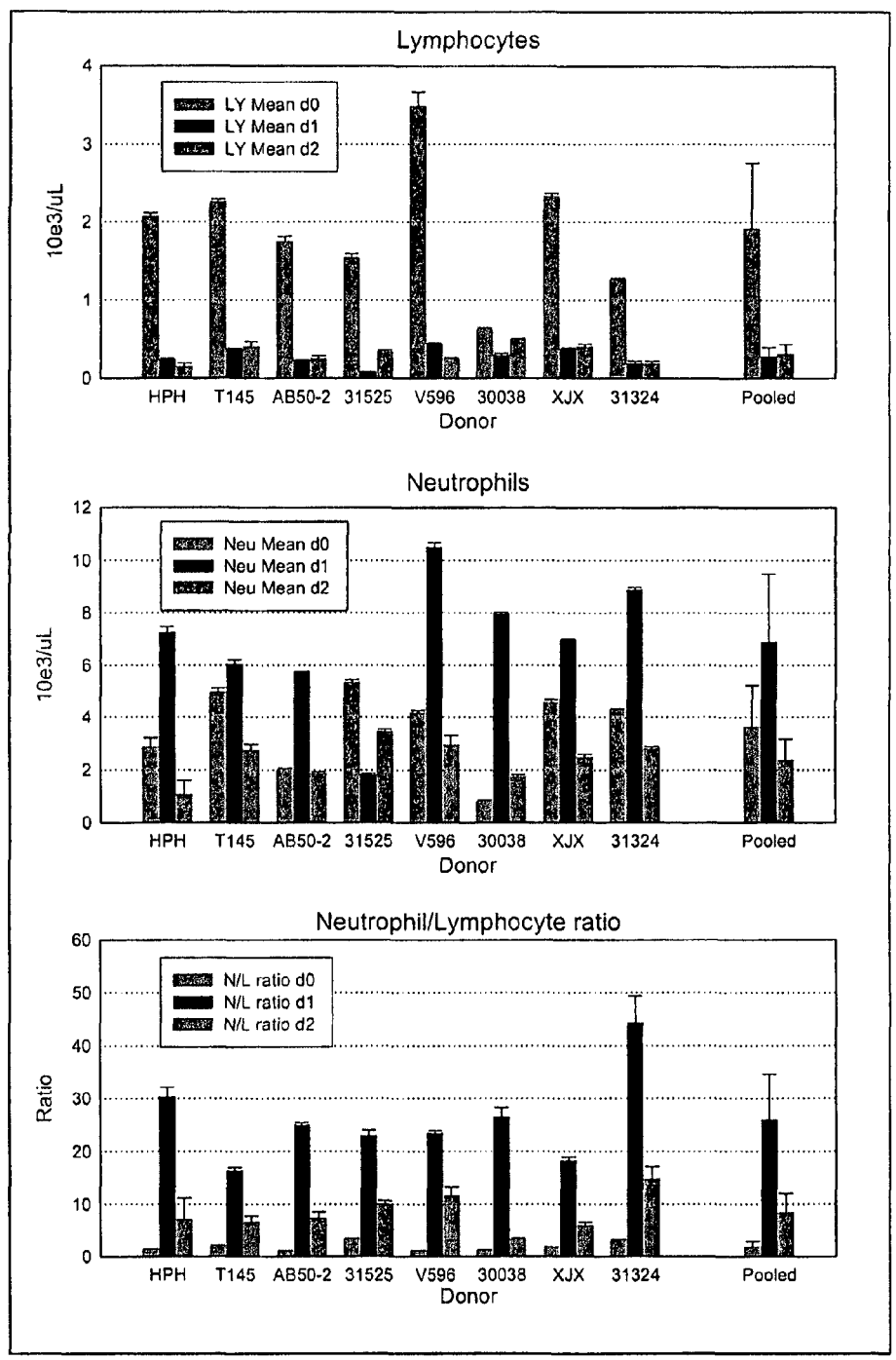
FIG. 17 shows hematological parameters from monkeys before and 1 and 2 days after 6.6 Gy whole-body gamma irradiation. Lymphocyte cell counts decrease following exposure to radiation and neutrophil cell counts increase. The ratio of neutrophils to lymphocytes ratio provides an enhanced ability to discriminate irradiated from non-irradiated from non-irradiated samples.

Blood cell counts with complete white blood cell differential from 8 rhesus monkeys were obtained before and at 24- and 48-h after radiation exposure (FIG. 17). Baseline peripheral blood-lymphocyte and neutrophil cell numbers fell between 0.6 to $3.5 \times 10^9 l^{-1}$ and 0.8 to $5.4 \times 10^9 l^{-1}$, respectively. Lymphocytes at 24- and 48-h after irradiation declined markedly among the cohort of 8 monkeys with a pooled mean decline value of 85.4 (±0.32) and 83.7 (±3.41)%, respectively. In 7 of 8 monkeys, the neutrophils at 24 h after irradiation increased with a pooled (n=8) mean increase value of 1.9-fold (±0.38). In 7 of 8 monkeys, neutrophils at 48 h after irradiation either returned to or fell below (65.7±12.6%; pooled before irradiation value) initial baseline levels.

The ratio of neutrophil to lymphocyte (N/L) cell numbers was also evaluated (FIG. 17). Baseline N/L values ranged from 1.15 to 3.46 with a pooled cohort value of 2.0 (±0.34). After irradiation the N/L value increased 13- (±2.66) and 4.23-fold (±0.95) at 24-h and 48-h, respectively, in the cohort (n=8) compared with the pre-irradiation value.

Amylase Measurements

Figure 18:
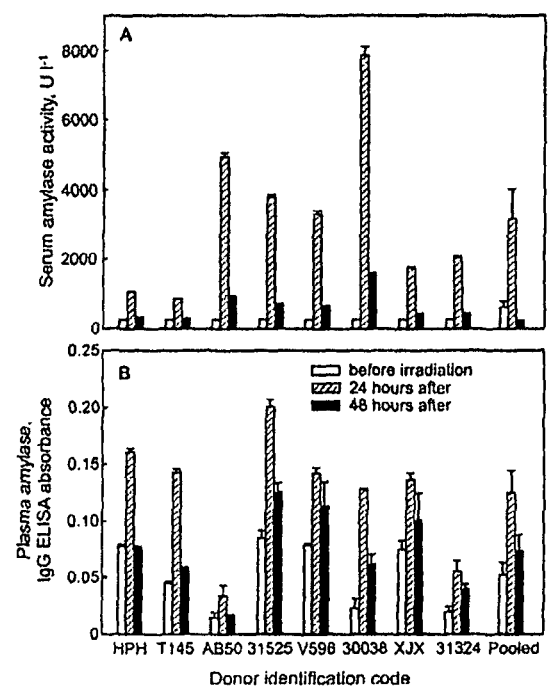
FIG. 18 shows radiation-responsive changes in serum amylase in monkey samples at 24 and 48 hours after and before exposure to $^{60}$Co gamma rays (6.5 Gy).

Serum amylase activity and plasma α-amylase protein content were measured before as well as 24- and 48-h after irradiation of monkeys (FIG. 18). Plasma α-amylase protein content baseline values ranged from 0.015 to 0.085 IgG ELISA absorbance with a pooled cohort mean value of 0.053 (±0.0106). In individual monkeys, radiation caused a 1.8- to 5.6-fold increase (pooled value of 2.73±0.44 fold) in plasma α-amylase protein content at 24 h relative to the individual baseline values. In 3 of 8 monkeys, α-amylase protein content was elevated (1.45 to 2.7 fold) 48 h after radiation. The pooled value of plasma α-amylase protein content in the cohort (n=8) was increased by 2.39- (±0.607) and 1.42-fold (±0.38) at 24 or 48 h, respectively, after radiation (FIG. 18) compared to the pooled cohort value.

Baseline serum amylase activity values ranged from 224 to 343 U $l^{-1}$ with a pooled cohort value of 267 (±16.68) U $l^{-1}$ (FIG. 18). In individual monkeys, radiation caused a 3.4- to 30.5-fold increase (pooled value of 12.3±3.26 fold) in plasma α-amylase protein content at 24 h relative to the individual baseline value. By 48 h after radiation, serum amylase activity decreased relative to peak values observed at 24 hr after radiation, with values ranging from 299 to 1557 U $l^{-1}$ and a pooled cohort value of 685 (±147.9) U $l^{-1}$.

Example 6

Non-Human Primate (Rhesus Macaques) In Vivo Radiation Model

Figure 19:
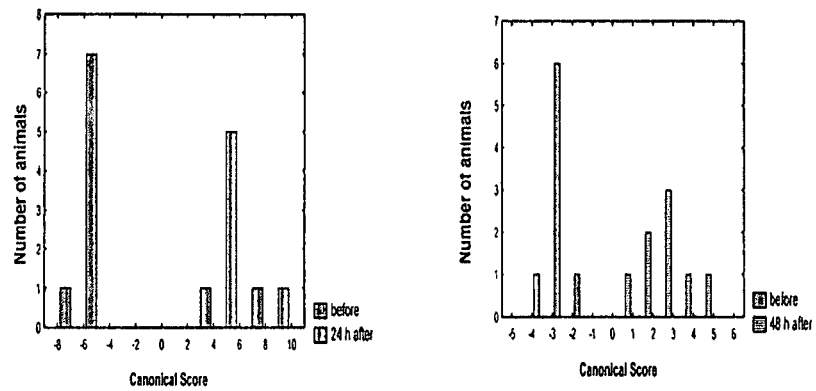
FIG. 19 shows discriminant analysis data for C-reactive protein, amylase activity, neutrophils, lymphocytes, and the ratio of neutrophils to lymphocytes from monkey samples: A) before and 1 day after, and B) before and 2 days after 6.6 Gy whole body gamma irradiation.

Blood samples from rhesus monkeys exposed to 6.5 Gy at several sampling time-points were obtained. The levels of C-reactive protein, amylase activity, neutrophils, lymphocytes, and the ratio of neutrophils to lymphocytes, were measured in the samples. The data was analyzed with use of multivariate discriminant analysis and established very successful separation of non-human primates groups: 100% discrimination power for animals with correct classification for separation between groups before and 24h and 48h after irradiation (FIG. 19). Clear separation of animals before and after irradiation can be seen.

Example 7

Dose-Response (Mus Musculus) in Vivo Radiation Model

Multiple Regression Analysis was used to develop dose-response relationships for multiple protein inductions for radiation dose assessment (FIG. 20). The general purpose of multiple regression is to learn more about the relationship between several independent variables (biomarkers) and a dependent variable (dose). Multiple regression procedures estimate a linear equation of the form:

$$Y=a+b1*X1+b2*X2+\ldots+bp*Xp$$

where Y variable (dose assessment) can be expressed in terms of a constant (a) and a slope (b) times the X variables (dose-response protein expression), p is a number of protein biomarkers in the model. The regression coefficients (or b coefficients) represent the independent contributions of each independent variable to the prediction of the dependent variable.

There is considerable individual variability in radiation response that makes the diagnostic utility of individual proteins limited in exposure dose assessment, but still feasible when analyzed according to multiple biomarkers pathway. To our knowledge, this is the first report of a dose-response calibration curve for multiple radiation-responsive protein biomarkers. Use of multiple protein targets, along with classic biodosimetric methodologies, is expected to enhance the prognostic utility of protein-based biomarkers approach for early assessment of severe radiation over-exposure.

While the foregoing specification teaches the principles of the invention, with examples provided for the purpose of illustration, it will be appreciated by one skilled in the art from reading this disclosure that various changes in form and detail can be made without departing from the true scope of the invention.

References Cited

Blakely et al., *Health Physics* 89(5):494-504, (2005)
Sine et al., *Military Medicine* 166(12):85-87, (2001)
Salter et al., *Public Protection from Nuclear, Chemical, and Biological Terrorism: Health Physics Society* 2004 Summer School: 481-488, (2004)
Hoffmann et al., *Strahlentherapy Onkology* 166 (10): 688-695 (1990)
Becciolini et al., *Phys. Med.* 17 (Suppl. 1): 185-186 (2001))
Bertho et al., *Int. J. Radiat. Biol.* 77(6):703-712 (2001)
Mal'tsev et al., *Dokl. Akad. Nauk. SSR* 239(3):750-752 (1978)
Koc et al., *Biol. Pharm. Bull.* 26(10):1494-1497 (2003)
Gartel et al., *Molecular Cancer Therapeutics* vol. 1, 639-649 (2002)
Bellido et al., *J Biol. Chem.* 273, 21137-21144 (1998)
Becciolini et al., *Strahlentherapie* 156, 69-72 (1980)
Becciolini et al., *Acta Radiol. [Oncol.]* 23, 9-14 (1984)
Becciolini et al., *Acta Oncologica* 26, 139-142 (1987)
Tomassi et al., *Strahlentherapie* 155:570-573 (1979)
Chen et al, *Radiation Research* 54:141-151 (1973)
Van Den Brenk et al., *Journal of Radiology* 42:688-700 (1969)
Wood et al., *Journal of Experimental Medicine* 111:601-609 (1960)

Tukachinski and Moiseeva, *Bulletin of Experimental Biology and Medicine* 52:48-52 (1961)
Mal'tsev et al., *Journal of Radiation Biology* 46(2): 152-8 (2006)
Goltry et al., *Radiation Research* 149(6):570-8 (1998)
Kalechman et al., *Immunopharmacology* 29(2):149-58 (1995)
Dainiak, *Exp. Hematol.* 30, 513-28 (2002)
Levina et al., *Gematol Transfuziol.* 38(9):5-8 (1993)
Reif et al., *Arch Biochem Biophys.* 264(1):238-43 (1988)
Torti F M and Torti S V, *Blood* 99(10): 3505-16 (2002)
Lipschitz et al., *N Eng J Med.* 290:1213-1216 (1974)
Koziol et al., *Clin Chem.* 47:1804-1810 (2001)
Torti S V and Torti F M, *Adv Inorg Biochem.* 10:1 19-137 (1994).
Torti S V et al., *J Biol Chem.* 263:12638-12 (1988)
Wei et al., *Biochem Biophys Res Commun.* 169:289-296 (1990)
Larsson et al., *Ups J Med Sci.* 103:231-236 (1998)
Cozzi et al., *J Biol Chem.* 275:25122-25129 (2000)
Thweatt et al., *Exp Gerontol.* 27:433-440 (1992)
Khattree, R. and Naik, D. Multivariate Data Reduction and Discrimination with SAS Software, SAS Institute Inc., Cary, N.C., SAS Press and John Wiley Sons Inc., 574 pp (2000).
SAS Institute, Inc., SAS/STAT®, Users Guide, Version 6, Cary, N.C.: SAS Institute Inc. (2000).
Lutgens et al., *Int J Radiat Oncol Biol Phys* 57(4): 1067-74 (2003)
Lutgens, et al. *Int J Radiat Oncol Biol Phys* 60(1): 275-85 (2004)

We claim:

1. A method for assessing radiation injury and exposure in a subject suspected of being exposed to radiation comprising
measuring the levels of at least three protein biomarkers in a test sample from the subject, wherein the at least three protein biomarkers are from different biological pathways and selected from the group consisting of salivary amylase, GADD45α, p21$^{Cip1/Waf1}$, p53, C-reactive protein, IL-6, Flt-3-ligand, TNF-α, Bax, Bcl-2, lipase, and citrulline,
correlating the levels of the at least three protein biomarkers with an assessment of radiation injury and exposure, and
determining that the subject has been exposed to radiation or has radiation injury if at least two protein biomarker levels are significantly elevated as compared to control levels or determining that the subject has not been exposed to radiation or has no radiation injury if all tested biomarkers are not elevated as compared to control levels wherein control levels are levels of the at least three protein biomarkers measured in a sample obtained from a subject not exposed to radiation.

2. The method of claim 1, wherein the at least three protein biomarkers include one or more selected from the group consisting of salivary amylase, C-reactive protein, and Flt-3-ligand.

3. The method of claim 1, wherein the at least three protein biomarkers comprise C-reactive protein, Flt-3-ligand, and salivary amylase.

4. The method of claim 1, wherein the at least three protein biomarkers comprise C-reactive protein and IL-6.

5. The method of claim 1, wherein the at least three protein biomarkers comprise salivary amylase and IL-6.

6. The method of claim 1, wherein the at least three protein biomarkers comprise salivary amylase, C-reactive protein, and IL-6.

7. The method of claim 1, wherein the at least three protein biomarkers comprise p53, salivary amylase, C-reactive protein, and IL-6.

8. The method of claim 1, wherein the at least three protein biomarkers comprise p21$^{Cip1/Waf1}$, salivary amylase, C-reactive protein, and IL-6.

9. The method of claim 1, wherein the subject is a mammal.

10. The method of claim 1, wherein the test sample is selected from the group consisting of saliva, blood, plasma, serum, skin, and urine.

11. The method of claim 1, wherein the levels of the at least three protein biomarkers are measured with an assay selected from the group consisting of ELISA, microsphere based immunoassay, lateral flow test strips, Western blots, and antibody-based dot blots.

12. The method of claim 1, wherein the levels of the at least three protein biomarkers are measured within 24 hours after suspected radiation exposure.

13. The method of claim 1, wherein the levels of the at least three protein biomarkers are measured within 48 hours after suspected radiation exposure.

14. The method of claim 1, further comprising measuring at least one hematological parameter in the test sample and correlating the hematological parameter and the levels of the at least three biomarkers with an assessment of radiation injury and exposure.

15. The method of claim 14, wherein the at least one hematological parameter is peripheral cell counts and/or Acute Phase Reaction biomarker levels.

16. The method of claim 15, wherein the peripheral blood counts comprise one or more of neutrophil levels, lymphocyte levels, platelet levels, and/or the ratio of neutrophil levels to lymphocyte levels.

17. The method of claim 1, wherein the levels of at least four protein biomarkers in a test sample from the subject are assessed.

18. A method for assessing radiation exposure and injury in a subject suspected of having been exposed to radiation, comprising:
measuring the levels of at least two protein biomarkers and at least one hematological parameter in a test sample from the subject, wherein the at least two protein biomarkers are from different biological pathways and selected from the group consisting of C-reactive protein, Flt-3-ligand and salivary amylase, correlating the levels of the at least two protein biomarkers and the at least one hematological parameter with an assessment of radiation exposure and injury; and
determining that the subject has been exposed to radiation or has radiation injury if at least any two of the protein biomarker levels and the at least one hematological parameter are significantly elevated as compared to control levels or determining that the subject has not been exposed to radiation or has no radiation injury if all tested protein biomarkers and hematological parameter(s) are not elevated as compared to control levels, wherein control levels are levels of the at least two protein biomarkers and of the at least one hematological parameter measured in a sample obtained from a subject not exposed to radiation.

* * * * *

UNITED STATES PATENT AND TRADEMARK OFFICE
CERTIFICATE OF CORRECTION

| | | |
|---|---|---|
| PATENT NO. | : 8,871,455 B2 | Page 1 of 1 |
| APPLICATION NO. | : 12/304566 | |
| DATED | : October 28, 2014 | |
| INVENTOR(S) | : William Blakely et al. | |

It is certified that error appears in the above-identified patent and that said Letters Patent is hereby corrected as shown below:

IN THE SPECIFICATION

Column 1, lines 7-9 delete:

"Work described herein may have been supported in part by USUHS/AFRRI intramural protocol BD-10. The U.S. Government may have certain rights in the invention."

and insert:

--This invention was made with government support under Intramural Protocol BD-10 awarded by Uniformed Services University. The government has certain rights in the invention.--

Signed and Sealed this
First Day of November, 2016

Michelle K. Lee
*Director of the United States Patent and Trademark Office*